(12) United States Patent
Patolsky et al.

(10) Patent No.: US 11,193,888 B2
(45) Date of Patent: Dec. 7, 2021

(54) METHOD AND SYSTEM FOR SEPARATING BIOMOLECULES FROM A MIXTURE CONTAINING SAME

(71) Applicant: Ramot at Tel-Aviv University Ltd., Tel-Aviv (IL)

(72) Inventors: Fernando Patolsky, Rehovot (IL); Vadim Krivitsky, Bney-Ayish (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 8 days.

(21) Appl. No.: 16/499,285

(22) PCT Filed: Mar. 29, 2018

(86) PCT No.: PCT/IL2018/050374
§ 371 (c)(1),
(2) Date: Sep. 29, 2019

(87) PCT Pub. No.: WO2018/178992
PCT Pub. Date: Oct. 4, 2018

(65) Prior Publication Data
US 2020/0025684 A1    Jan. 23, 2020

Related U.S. Application Data

(60) Provisional application No. 62/478,075, filed on Mar. 29, 2017.

(51) Int. Cl.
*G01N 21/64* (2006.01)
*G01N 21/33* (2006.01)
(Continued)

(52) U.S. Cl.
CPC ......... *G01N 21/6428* (2013.01); *G01N 21/33* (2013.01); *G01N 21/49* (2013.01); *G01N 33/582* (2013.01); *B82Y 15/00* (2013.01)

(58) Field of Classification Search
CPC .... G01N 21/6428; G01N 21/33; G01N 21/49; G01N 33/582; B82Y 15/00
See application file for complete search history.

(56) References Cited

U.S. PATENT DOCUMENTS

| 7,619,290 B2 | 11/2009 | Lieber et al. |
| 2009/0061451 A1* | 3/2009 | Achim ............... G01N 33/5438 435/6.11 |

(Continued)

FOREIGN PATENT DOCUMENTS

| WO | WO 2011/000443 | 1/2011 |
| WO | WO 2015/059704 | 4/2015 |

(Continued)

OTHER PUBLICATIONS

Huang et al., "Controllable synthesis of brached ZnO/Si nanowire arrays with hierarchical structure," 2014, Nanoscale Research Letters, vol. 9, No. 328, 9 pages. (Year: 2014).*

(Continued)

*Primary Examiner* — Kiho Kim

(57) ABSTRACT

A system featuring a substrate and a multiplicity of nanostructures arranged on the substrate is provided. At least one portion of the nanostructures feature a capturing moiety covalently attached to a surface thereof and at least another portion of the nanostructures, which can be the same or different from the first portion, feature a light-activatable moiety covalently attached to a surface thereof. The capturing moiety is such that selectively interacts with an analyte, and the light-activatable moiety generates, upon exposure to light, a reactive moiety that interferes with an interaction of the capturing moiety and the analyte. Further provided are systems featuring a substrate and a multiplicity of nanostructures aligned generally vertically to the substrate, at least a portion of these nanostructures being branched nano- (Continued)

structures. Uses of the systems in extracting, and optionally identifying, the analyte from a sample are also provided.

25 Claims, 16 Drawing Sheets

(51) Int. Cl.
G01N 21/49 (2006.01)
G01N 33/58 (2006.01)
B82Y 15/00 (2011.01)

(56) References Cited

U.S. PATENT DOCUMENTS

| | | | |
|---|---|---|---|
| 2010/0022012 | A1 | 1/2010 | Lieber et al. |
| 2010/0325073 | A1 | 12/2010 | Haick |
| 2011/0088511 | A1* | 4/2011 | Jalaledin et al. ..... B22F 1/0025 |

FOREIGN PATENT DOCUMENTS

| | | |
|---|---|---|
| WO | WO 2017/098517 | 6/2017 |
| WO | WO 2018/037406 | 3/2018 |
| WO | WO 2018/178982 A9 | 10/2018 |
| WO | WO 2018/178992 | 10/2018 |

OTHER PUBLICATIONS

Figure 1:
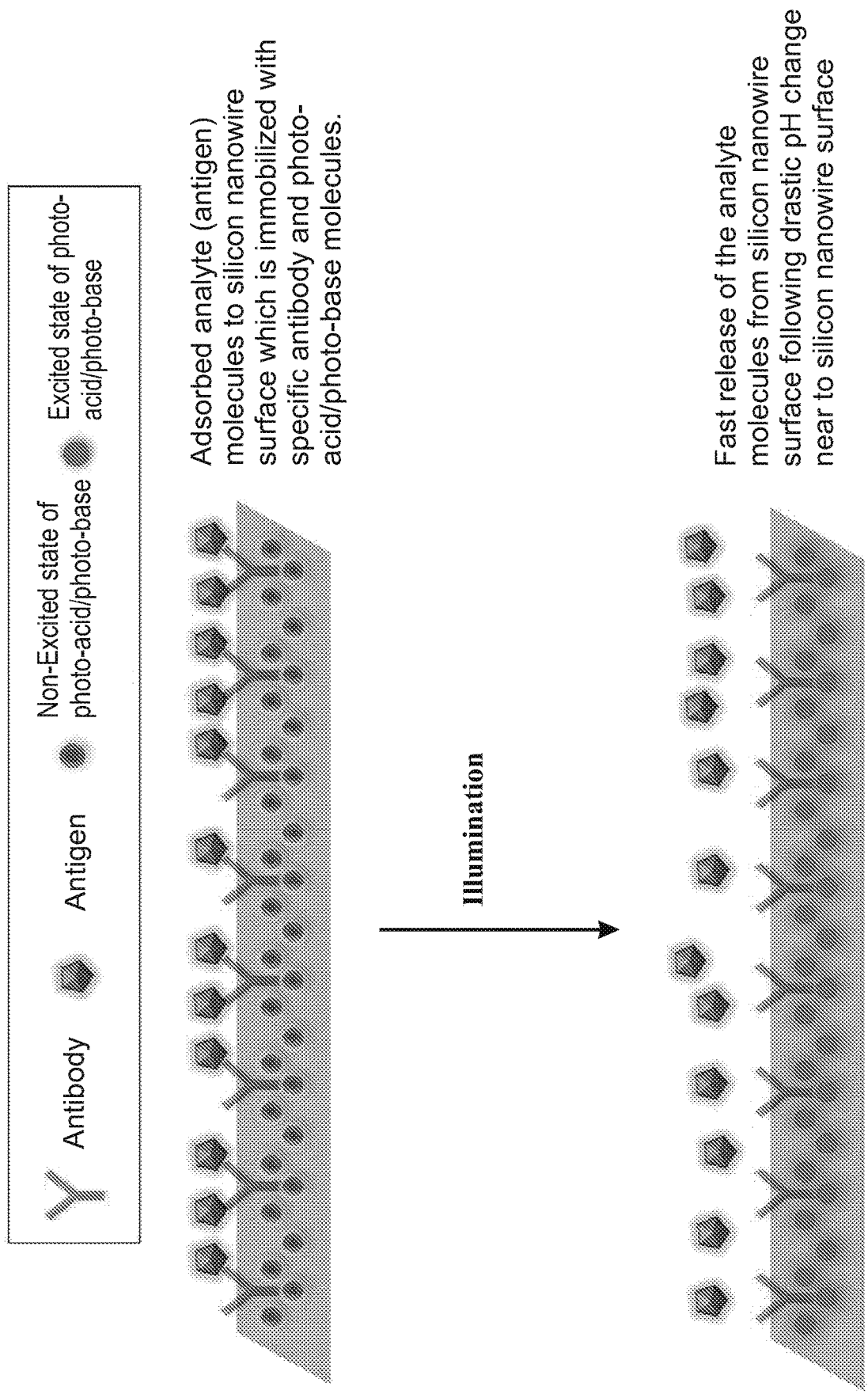

International Preliminary Report on Patentability dated Oct. 10, 2019 From the International Bureau of WIPO Re. Application No. PCT/IL2018/050374. (8 Pages).
International Search Report and the Written Opinion dated Jul. 10, 2018 From the International Searching Authority Re. Application No. PCT/IL2018/050374. (12 Pages).
Borberg et al. "Light-Controlled Selective Collection-and-Release of Biomolecules by An On-Chip Nanostructured Device", Nano Letters, 19(9): 5868-5878, Published Online Aug. 12, 2019 & Supporting Information.
Chen et al. "Silicon Nanowire Field-Effect Transistor-Based Biosensors for Biomedical Diagnosis and Cellular Recording Investigation", Nano Today, 6(2): 131-154, Available Online Mar. 8, 2011.
Clavaguera et al. "Sub-PPM Detection of Nerve Agents Using Chemically Functionalized Silicon Nanoribbon Field-Effect Transistors", Angewandte Chemie International Edition, 49: 4063-4066, 2010.
Cui et al. "Nanowire Nanosensors for Highly Sensitive and Selective Detection of Biological and Chemical Species", Science, 293: 1289-1292, Aug. 17, 2001.
Duan et al. "Intracellular Recordings of Action Potentials by An Extracellular Nanoscale Field-Effect Transistor", Nature Nanotechnology, 7(3): 174-179, Published Online Dec. 18, 2011.
Jiang et al. "ITO[Alpha]Cu2S tunnel Junction Nanowire Array as Efficient Counter Electrode for Quantum-Dot-Sensitized Solar Cells", Nano Letters, 14(1): 365-372, Published Online Dec. 13, 2013. Supporting Information Table 52.
Kosaka et al. "Detection of Cancer Biomarkers in Serum Using A Hybrid Mechanical and Optoplasmonic Nanosensor", Nature Nanotechnology, 9(12): 1047-1053, Published Online Nov. 2, 2014.
Krivitsky et al. "Si Nanowires Forest-Based On-Chip Biomolecular Filtering, Separation and Preconcentration Devices: Nanowires Do It All", Nano Letters, 12(9): 4748-4756, Aug. 2, 2012. Abstract.
Li et al. "Sequence-Specific Label-Free DNA Sensors Based on Silicon Nanowires", Nano Letters, 4(2): 245-247, Feb. 11, 2004.
Lu et al. "A Nano-Ni Based Ultrasensitive Nonenzymatic Electrochemical Sensor for Glucose: Enhancing Sensitivity Through A Nanowire Array Strategy", Biosensors and Bioelectronics, 25(1): 218-223, Published Online Jul. 7, 2009.
Lu et al. "Enzyme-Functionalized Gold Nanowires for the Fabrication of Biosensors", Bioelectrochemistry, 71(2): 211-216. Published Online Jun. 14, 2007.
McAlpine et al. "Highly Ordered Nanowire Arrays on Plastic Substrates for Ultrasensitive Flexible Chemical Sensors", Nature Materials, 6(5): 239-384, Published Online Apr. 22, 2007.
Patolsky et al. "Electrical Detection of Single Viruses", Proc. Natl. Acad. Sci. USA, PNAS, 101(39): 14017-14022, Sep. 28, 2004.
Patolsky et al. "Nanowire-Based Biosensors", Analytical Chemistry, 78: 4260-4269, Jul. 1, 2006.
Peretz-Soroka et al. "Manipulating and Monitoring On-Surface Biological Reactions by Light-Triggered Local pH Alterations", Nano Letters, 15(7): 4758-4768, Jun. 18, 2015.
Piao et al. "Enzyme Incorporated Microfluidic Device for In-Situ Glucose Detection in Water-in-Air Microdroplets", Biosensors and Bioelectronics, 65: 220-225, Available Online Oct. 18, 2014.
Revzin et al. "Fabrication of Poly(Ethylene Glycol) Hydrogel Microstructures Using Photolithography", Langmuir, 17(18): 5440-5447, Published on Web Jul. 18, 2001.
Shao et al. "Silicon Nanowire Sensors for Bioanalytical Applications: Glucose and Hydrogen Peroxide Detection", Advanced Functional Materials, 15(9): 1478-1482, Sep. 2005.
Stern et al. "Label-Free Biomarker Detection From Whole Blood", Nature Nanotechnology, 5(2): 138-142, Published Online Dec. 13, 2009.
Stern et al. "Semiconducting Nanowire Field-Effect Transistor Biomolecular Sensors", IEEE Transactions on Electron Devices, 55(11): 3119-3130, Nov. 2008.
Su et al. "A Silicon Nanowire-Based Electrochemical Sensor With High Sensitivity and Electrocatalytic Activity", Particle Particle Systems Characterization, 30(4): 326-331, Apr. 2013.
Timko et al. "Electrical Recording From Hearts With Flexible Nanowire Device Arrays", Nano Letters, 9(2):914-918, Feb. 2009.
Tyagi et al. "Patternable Nanowire Sensors for Electrochemical Recording of Dopamine", Analytical Chemistry, 81(24): 9979-9984, Dec. 15, 2009.
Yang et al. "Gold Nanoparticle Modified Silicon Nanowires as Biosensors", Nanotechnology, 17(11): S276-S279, May 19, 2006.
Zhang et al. "Hierarchical Nanowire Arrays as Three-Dimensional Fractal Nanobiointerfaces for High Efficient Capture of Cancer Cells", Nano Letters, 16(1): 766-722, Published online Dec. 15, 2015. Fig. 1.
Zheng et al. "Multiplexed Electrical Detection of Cancer Markers With Nanowire Sensor Arrays", Nature Biotechnology, 23(10): 1294-1301.
Supplementary European Search Report and the European Search Opinion dated Nov. 13, 2020 From the European Patent Office Re. Application No. 18776148.1. (10 Pages).
Krivitsky et al. "Antigen-Dissociation From Antibody-Modified Nanotransistor Sensor Arrays as A Direct Biomarker Detection Method in Unprocessed Biosamples", Nano Letters, XP055592675, 16(10): 6272-6281, Published Online Sep. 6, 2016.
Noor et al. "Silicon Nanowires as Field-Effect Transducers for Biosensor Development: A Review", Analytica Chimica Acta, XP028648847, 825: 1-25, Available Online May 15, 2014.

\* cited by examiner

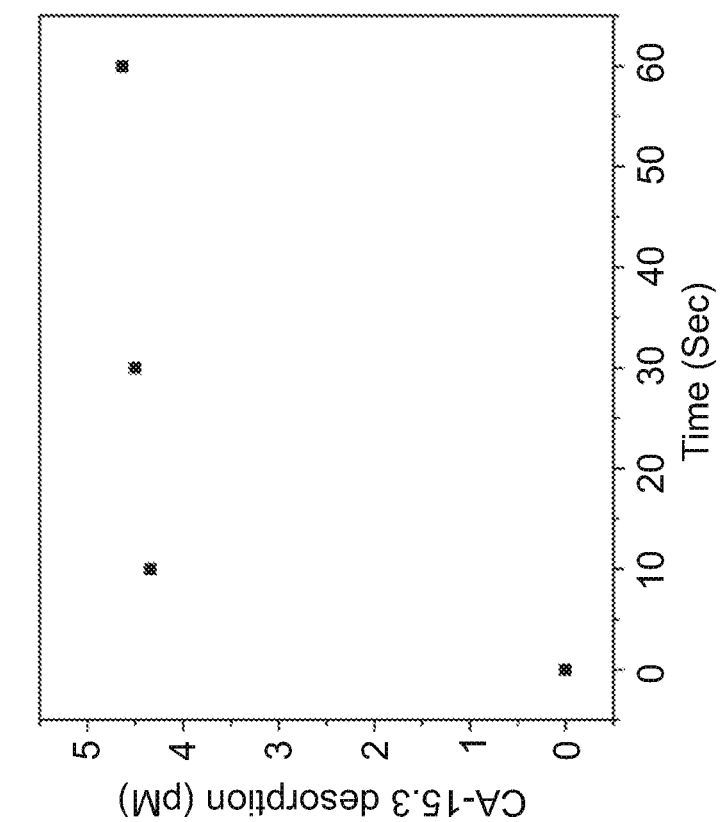
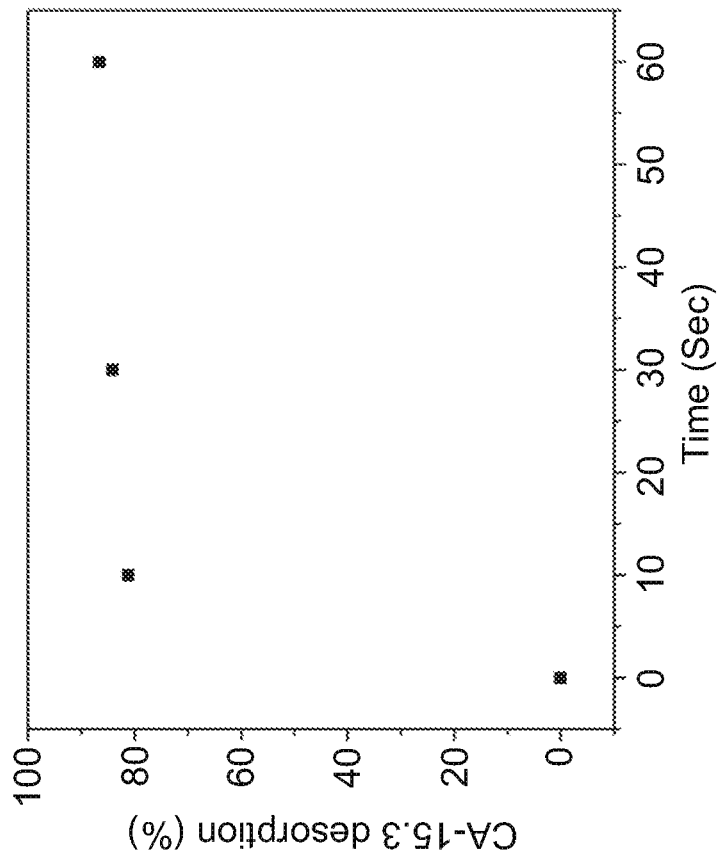
FIG. 7A
FIG. 7B

METHOD AND SYSTEM FOR SEPARATING BIOMOLECULES FROM A MIXTURE CONTAINING SAME

RELATED APPLICATIONS

This application is a National Phase of PCT Patent Application No. PCT/IL2018/050374 having International filing date of Mar. 29, 2018, which claims the benefit of priority under 35 USC § 119(e) of U.S. Provisional Patent Application No. 62/478,075 filed on Mar. 29, 2017. The contents of the above applications are all incorporated by reference as if fully set forth herein in their entirety.

FIELD AND BACKGROUND OF THE INVENTION

The present invention, in some embodiments thereof, relates to separation/extraction of analytes, and, more particularly, but not exclusively, to systems usable in, and methods for, selectively separating analytes of interest (e.g., biomolecules such as biomarkers) from a liquid mixture containing same, for example, from a biological sample.

The development of efficient bio-molecular separation and purification techniques is of high importance in modern genomics, proteomics, and bio-sensing areas, primarily because most bio-samples are mixtures of high diversity and complexity. Most of the currently practiced techniques lack the capability to rapidly and selectively separate and concentrate specific target molecules (e.g., metabolites, proteins) from a complex bio-sample, and are difficult to integrate with lab-on-a-chip sensing devices.

Semiconducting nanowires are known to be extremely sensitive to chemical species adsorbed on their surfaces. For a nanowire device, the binding of a charged analyte to the surface of the nanowire leads to a conductance change, or a change in current flowing through the wires.

The 1D (one-dimensional) nanoscale morphology and the extremely high surface-to-volume ratio make this conductance change to be much greater for nanowire-based sensors versus planar FETs (field-effect transistors), increasing the sensitivity to a point that single molecule detection is possible.

Nanowire-based field-effect transistors (NW-FETs) have therefore been recognized in the past decade as powerful potential new sensors for the detection of chemical and biological species. See, for example, Patolsky et al., Analytical Chemistry 78, 4260-4269 (2006); Stern et al., IEEE Transactions on Electron Devices 55, 3119-3130 (2008); Cui et al., Science 293, 1289-1292 (2001); Patolsky et al. Proceedings of the National Academy of Sciences of the United States of America 101, 14017-14022 (2004), all being incorporated by reference as if fully set forth herein.

Studies have also been conducted with nanowire electrical devices for the simultaneous multiplexed detection of multiple biomolecular species of medical diagnostic relevance, such as DNA and proteins [Zheng et al., Nature Biotechnology 23, 1294-1301 (2005); Timko et al., Nano Lett. 9, 914-918 (2009); Li et al., Nano Lett. 4, 245-247 (2004)].

Antibody/enzyme nanowire FET devices which target metabolites via binding affinity have been disclosed in, for example, Lu et al. *Bioelectrochemistry* 2007, 71(2): 211-216; Patolsky et al. Nanowire-based biosensors. *Anal Chem* 2006, 78(13): 4260-4269; and Yang et al. *Nanotechnology* 2006, 17(11): S276-S279.

Electrochemically-sensitive nanowire sensors for detecting metabolites by oxidative reactions have been disclosed in, for example, Lu et al. Biosens Bioelectron 2009, 25(1): 218-223; Shao et al. Adv Funct Mater 2005, 15(9): 1478-1482; Su et al. Part Part Syst Char 2013, 30(4): 326-331; and Tyagi et al. Anal Chem 2009, 81(24): 9979-9984.

U.S. Pat. No. 7,619,290, U.S. Patent Application having publication No. 2010/0022012, and corresponding applications, teach nanoscale devices composed of, inter alia, functionalized nanowires, which can be used as sensors.

Clavaguera et al. describes a method for sub-ppm detection of nerve agents using chemically functionalized silicon nanoribbon field-effect transistors [Clavaguera et al., Angew. Chem. Int. Ed. 2010, 49, 1-5].

$SiO_2$ surface chemistries were used to construct a 'nano-electronic nose' library, which can distinguish acetone and hexane vapors via distributed responses [Nature Materials Vol. 6, 2007, pp. 379-384].

U.S. Patent Application having Publication No. 2010/0325073 discloses nanodevices designed for absorbing gaseous NO. WO 2011/000443 describes nanodevices which utilize functionalized nanowires for detecting nitro-containing compounds.

Duan et al. [Nature Nanotechnology, Vol. 7, 2012, pp. 174-179] describes a silicon nanowire FET detector and an electrically insulating SiO2 nanotube that connects the FET to the intracellular fluid (the cytosol). When there is a change in transmembrane potential (mV), the varying potential of the cytosol inside the nanotube gives rise to a change in the conductance G of the FET.

Kosaka et al. [Nature Nanotechnology, Vol. 9, 2014, pp. 1047-1053] discloses detection of cancer biomarkers in serum using surface-anchored antibody.

Krivitsky et al. [Nano letters 2012, 12(9): 4748-4756] describe an on-chip all-SiNW filtering, selective separation, desalting, and preconcentration platform for the direct analysis of whole blood and other complex biosamples. The separation of required protein analytes from raw bio-samples is performed using an antibody-modified roughness-controlled SiNWs forest of ultra-large binding surface area, followed by the release of target proteins in a controlled liquid media, and their subsequent detection by SiNW-based FETs arrays fabricated on the same chip platform.

WO 2015/059704 discloses an integrated microfluidic nanostructure sensing system, comprised of one or more sensing compartments featuring a redox-reactive nanostructure FET array which is in fluid communication with one or more sample chambers. This system has been shown to perform multiplex real-time monitoring of cellular metabolic activity in physiological solutions, and was demonstrated as an efficient tool in promoting the understanding of metabolic networks and requirements of cancers for personalized medicine.

Revzin et al. Langmuir 2001, 17, 5440-5447, describe cross-linked hydrogel microstructures based upon poly(ethylene glycol) diacrylates, dimethacrylates, and tetraacrylates patterned photolithographically on silicon or glass substrates, and further describe arrays of such hydrogel disks containing an immobilized protein conjugated to a pH sensitive fluorophore.

Piao et al., Biosensors and Bioelectronics 65 (2015) 220-225, describe droplet generating microfluidic systems which can serve as a sensitive and in-situ glucose monitoring system using water-in-air droplets in an enzyme incorporated micro-fluidic device. The system is made of a thin film structure of a glucose oxidase (GOx) enzyme immobilized hydrogel constructed in the middle of the microfluidic channel, and nanoliter scaled water-in-air droplets which contain a glucose sample, horseradish peroxidase (HRP), and an Amplex Red substrate, generated by flow focusing of water phase with air. While the droplets pass through the enzyme trapped hydrogel, a GOx mediated catalytic reaction with glucose occurs, and fluorescent resorufin products are formed in the droplets.

Peretz-Soroka et al., Nano Lett. 2015, 15, 4758-4768, describe photoactive molecularly modified nanowires, integrated in a FET device which provide a light-controlled fine modulation of the surface pH of the device, and show that such structures can be utilized for modulating the on-surface pH, by intensity-controlled light stimulus, and for simultaneously and locally controlling and monitoring pH-sensitive biological reactions on the nanodevices surfaces, such as the local activation and inhibition of proteolytic enzymatic processes, and dissociation of antigen-antibody binding interactions.

Additional background art includes, for example, Chen et al., Nano Today (2011) 6, 131-54, and references cited therein; Stern et al., Nature Nanotechnology, 2009; WO 2017/098517 and WO 2018/037406.

SUMMARY OF THE INVENTION

The present inventors have devised and successfully practiced a system is made of a multiplicity of elongated nanostructures featuring a rough and/or porous surface, modified by a capturing moiety that selectively interacts with an analyte, and by a light-activatable moiety, which, when activated, induces a release of the analyte, thereby allowing a direct extraction and optionally further analysis of analytes from liquid mixtures containing same.

Embodiments of the present invention provide a light-controlled system for filtering, selectively separating, desalting, and/or pre-concentrating liquid mixtures and for a controlled release platform, usable in direct analysis of complex liquid mixtures such as whole blood and other complex biosamples.

According to an aspect of some embodiments of the present invention there is provided a system comprising a substrate and a multiplicity of nanostructures arranged on the substrate at a density of at least 100,000 nanostructures per 1 cm$^2$, each nanostructure in at least a first portion of the nanostructures featuring a capturing moiety covalently attached to a surface thereof and each nanostructure in at least a second portion of the nanostructures featuring a light-activatable moiety covalently attached to a surface thereof, wherein the capturing moiety selectively interacts with an analyte, and the light-activatable moiety generates, upon exposure to light, a reactive moiety that interferes with an interaction of the capturing moiety and the analyte.

According to some of any of the embodiments described herein, at least one of the nanostructures has both the capturing moiety and the light-activatable moiety covalently attached to a surface thereof.

According to some of any of the embodiments described herein, activating the light-activatable moiety comprises exposing the system to light at a wavelength that generates the reactive moiety.

According to some of any of the embodiments described herein, the reactive moiety is such that induces a release of at least 20% of molecules of the analyte that interact with the capturing moieties in 10 minutes.

According to some of any of the embodiments described herein, the analyte is a biomarker.

According to some of any of the embodiments described herein, the capturing moiety is a first member of an affinity pair and the analyte is a second member of the affinity pair.

According to some of any of the embodiments described herein, the affinity pair is selected from an antigen-antibody pair, a receptor-ligand pair, an enzyme-substrate pair, a streptavidin-biotin pair, a protein-cofactor pair, a protein-protein pair, and pairs of complementary oligonucleotides, or of complementary oligonucleotide-peptide nucleic acid.

According to some of any of the embodiments described herein, the capturing moiety is an antibody and the analyte selectively interacts with the antibody.

According to some of any of the embodiments described herein, the analyte is an antigen.

According to some of any of the embodiments described herein, the capturing moiety and the analyte feature a pH-dependent dissociation constant.

According to some of any of the embodiments described herein, the light-activatable moiety generates, upon the exposure to light, a reactive moiety that induces a change in protons concentration in proximity to the at least a portion of the nanostructures that features the capturing moiety.

According to some of any of the embodiments described herein, the light-activatable moiety generates, upon the exposure to light, protons.

According to some of any of the embodiments described herein, the elongated nanostructures are generally parallel to each other.

According to some of any of the embodiments described herein, the elongated nanostructures are aligned generally vertically to the substrate.

According to some of any of the embodiments described herein, the elongated nanostructures comprise nanowires.

According to some of any of the embodiments described herein, an average length of the nanostructures ranges from 10 nm to 500 microns.

According to some of any of the embodiments described herein, an average diameter of the nanostructures ranges from 10 nm to 30 microns.

According to some of any of the embodiments described herein, an average inter-distance between the nanostructures ranges from 10 nm to 10000 nm.

According to some of any of the embodiments described herein, the nanostructures comprise silicon.

According to some of any of the embodiments described herein, at least a portion of the nanostructures comprises branched nanostructures.

According to an aspect of some embodiments of the present invention there is provided a system as described herein in any of the respective embodiments and any combination thereof, for use in extracting the analyte from a liquid containing same.

According to some of any of the embodiments described herein, the extracting comprises contacting the liquid with the system and exposing the system to light at a wavelength that generates the reactive moiety.

According to some of any of the embodiments described herein, the liquid is a biological sample.

According to some of any of the embodiments described herein, the system further comprises a sensing element or system in fluid communication therewith.

According to some of any of the embodiments described herein, the sensing element or system comprises a nanostructure having covalently attached thereto the capturing moiety and is configured such that upon interaction of the capturing moiety and the analyte, a detectable signal which is indicative of a presence and/or level of the analyte is generated.

According to some of any of the embodiments described herein, the system is for use in extracting the analyte from a liquid sample containing same and determining a presence and/or level of the analyte in the liquid sample.

According to an aspect of some embodiments of the present invention there is provided a method of extracting an analyte from a liquid sample containing same, the method comprising:

contacting the liquid sample with the system of any one of claims 1-20 to thereby obtain a system having the analyte adsorbed to the nanostructures; and exposing the system to light at a wavelength that generates the reactive moiety.

According to some of any of the embodiments described herein, the method comprises during the exposing, contacting the system with an aqueous solution, to thereby obtain an aqueous solution containing the analyte.

According to some of any of the embodiments described herein, the exposing is for a time period that ranges from 1 to 1000, or from 1 to 500, or from 1 to 100, seconds.

According to some of any of the embodiments described herein, the method further comprises, subsequent to contacting the liquid sample with the system, washing the system with an aqueous solution (also referred to herein as a sensing solution or a sensing buffer).

According to some of any of the embodiments described herein, the contacting the liquid with the system is for a time period that ranges from 1 to 180 minutes, or from 10 to 120 minutes.

According to some of any of the embodiments described herein, the light-activatable moiety is such that upon 10 minutes of the exposing, at least 20% of the adsorbed analyte molecules are desorbed.

According to some of any of the embodiments described herein, the liquid is a biological sample.

According to some of any of the embodiments described herein, a concentration of the analyte in the liquid is less than 1 mM, or lower than 1 µM, or lower than 1 nM, or lower than 1 pM.

According to an aspect of some embodiments of the present invention there is provided a method of determining a presence and/or a level of an analyte in a liquid sample, the method comprising:

subjecting the liquid to the method as described herein in any of the respective embodiments and any combination thereof; and contacting the aqueous solution obtained upon the exposing with a sensing system configured for identifying and/or determining a presence and/or level of the analyte.

According to some of any of the embodiments described herein, the sensing element or system is as described herein in any of the respective embodiments.

According to an aspect of some embodiments of the present invention there is provided a system comprising a substrate and a multiplicity of nanostructures aligned generally vertically to the substrate at a density of at least 100,000 nanostructures per 1 $cm^2$, at least a portion of the nanostructures are branched nanostructures.

According to some of any of the embodiments described herein, each of the branched nanostructures independently comprises from 10 to 1,500,000 branches.

According to some of any of the embodiments described herein, an average length of each branch independently ranges from 5 to 40000 nm.

According to some of any of the embodiments described herein, an average diameter of the branched nanostructures independently ranges from 2 to 200 nm.

According to some of any of the embodiments described herein, each nanostructure in at least a portion of the nanostructures has a capturing moiety covalently attached to a surface thereof, the capturing moiety selectively interacts with an analyte. According to some of any of the embodiments described herein, each nanostructure in at least a portion of the nanostructures has a light-activatable moiety covalently attached to a surface thereof.

According to some of any of the embodiments described herein, the system is for use in extracting the analyte from a liquid sample containing same, and optionally for releasing the analyte upon exposure to light and further analyzing it by means of a sensing element or system as described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 presents a schematic representation of light-controlled fast release of analyte molecules from silicon nanowire surface.

Figure 2:
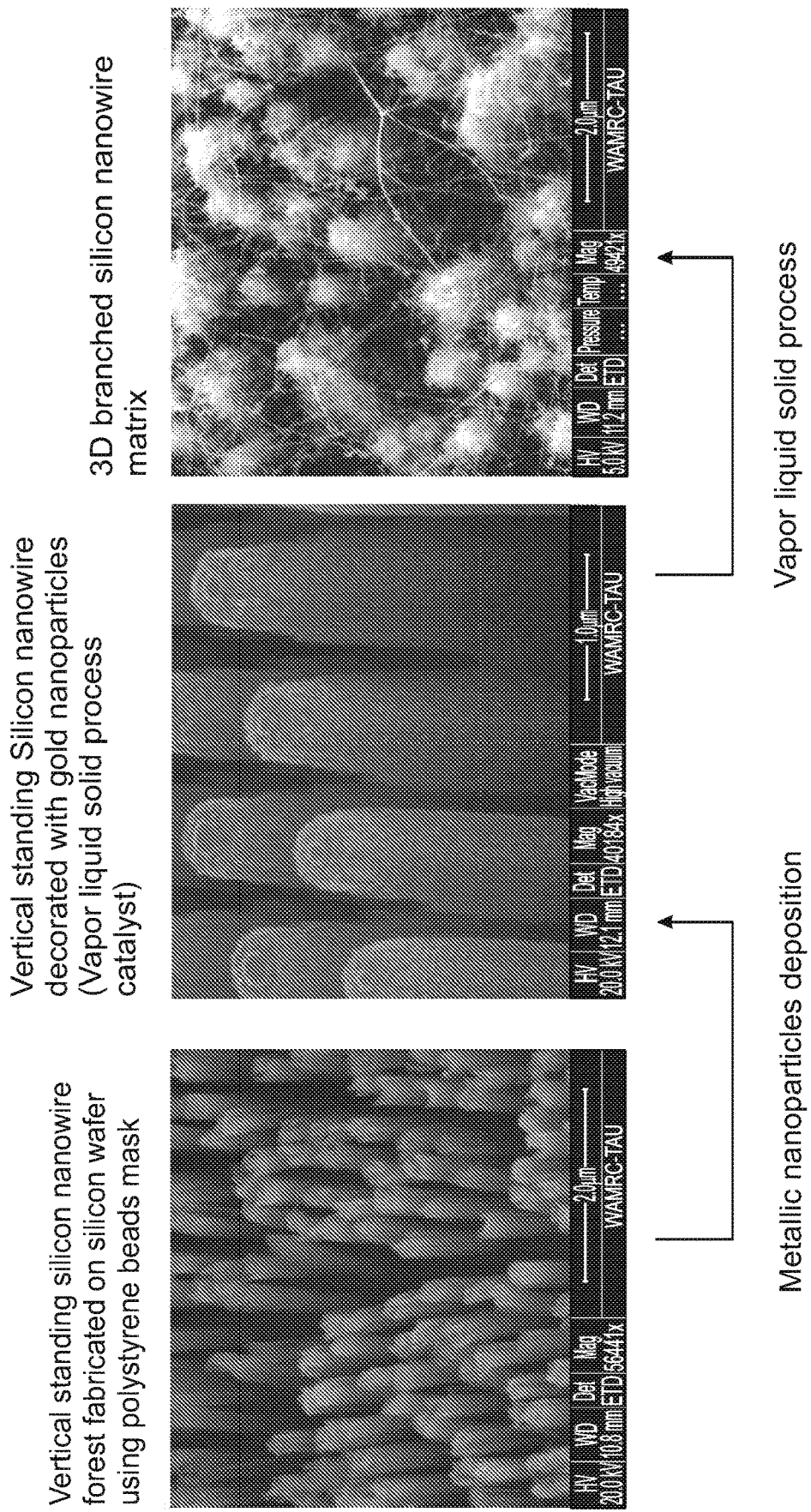

FIG. 2 presents SEM images of SiNWF (left), SiNWF in which gold nanoparticles are deposited on the nanowires' surface (middle), and of the obtained 3D branched SiNW matrix.

Figure 3B:
Figure 3A:
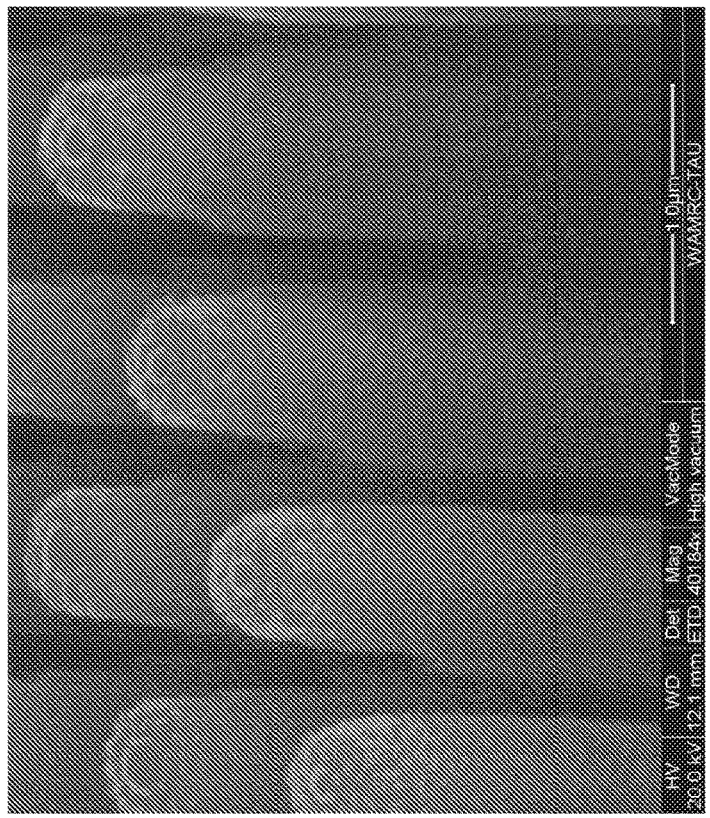
Figure 4B:
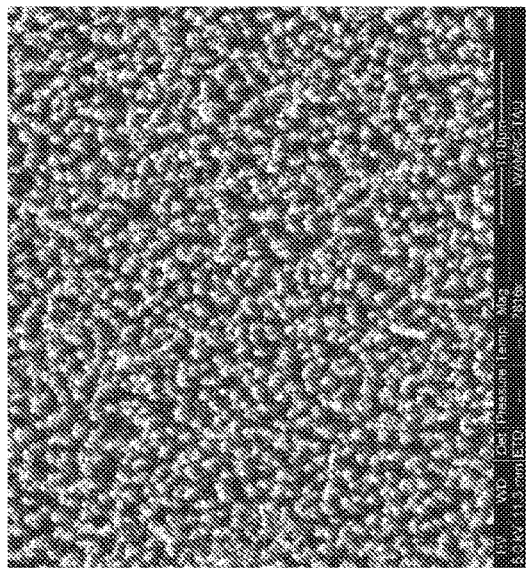
Figure 4D:
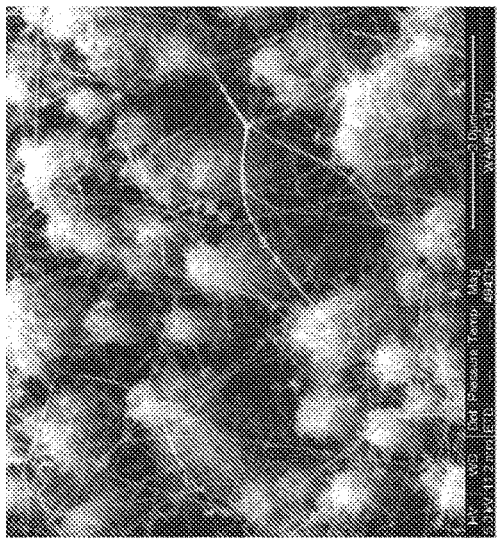
Figure 4A:
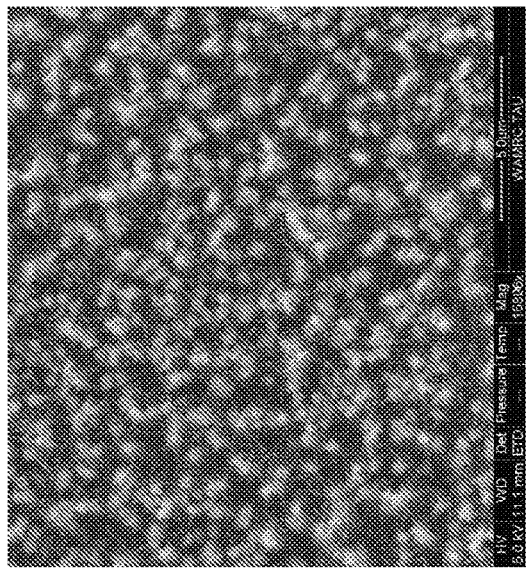
Figure 4C:
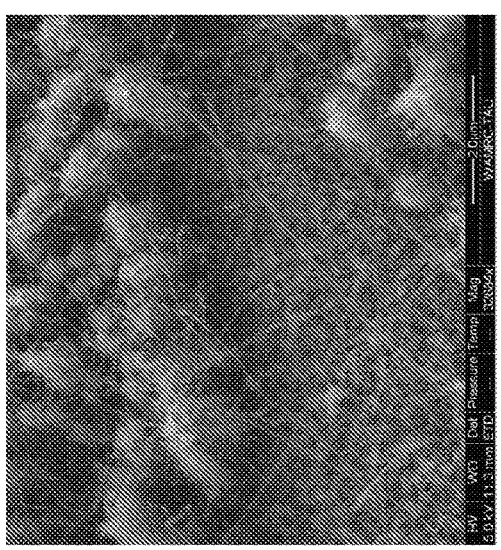

FIGS. 3A-B present SE (FIG. 3A) and BSE (FIG. 3B) images of SiNWF in which gold nanoparticles are deposited on the nanowires' surface.

FIGS. 4A-D present SE images of Branched Si Nanowires Forest (BSiNWF) at different magnifications.

Figure 5B:
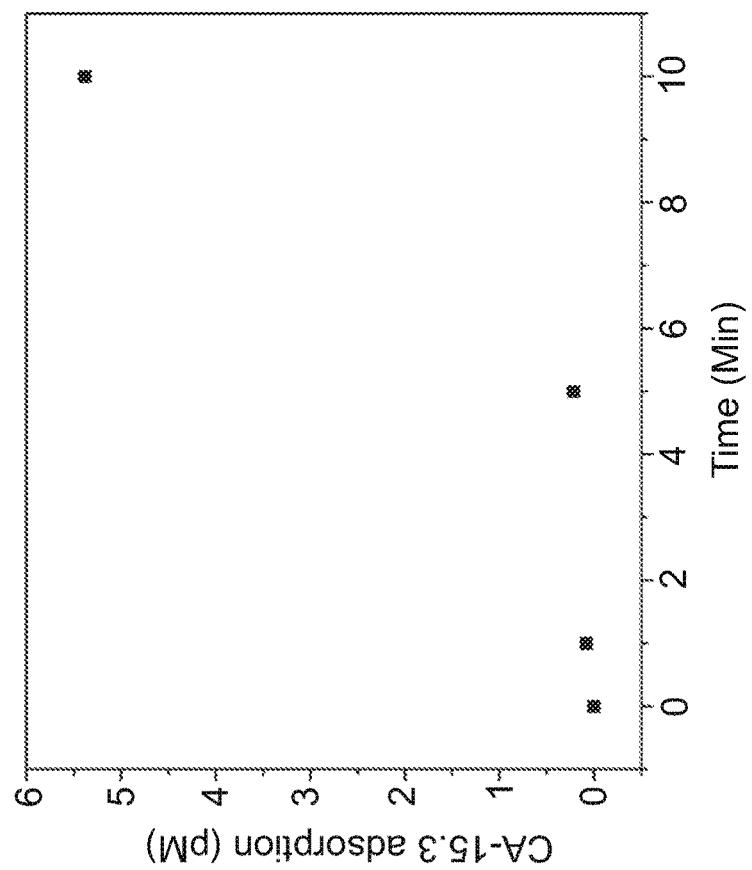
Figure 5A:
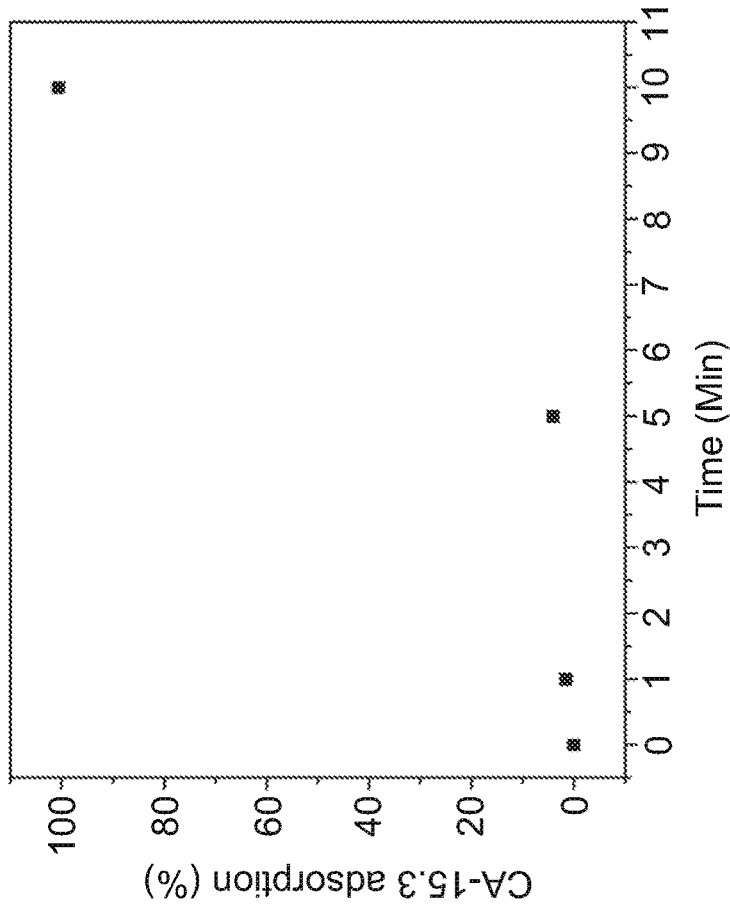

FIGS. 5A-B present the data obtained for adsorption of CA 15-3 on anti-CA 15-3- and HTPS-modified SiNW forest, from a solution containing 5.35 pM of the antigen in the sensing buffer as a function of incubation time, by percents (%) of the adsorbed antigen out of the total amount of the antigen in the solution (FIG. 5A) and by the concentration of the adsorbed antigen out of the total amount of the antigen in the solution (FIG. 5B).

Figure 6:
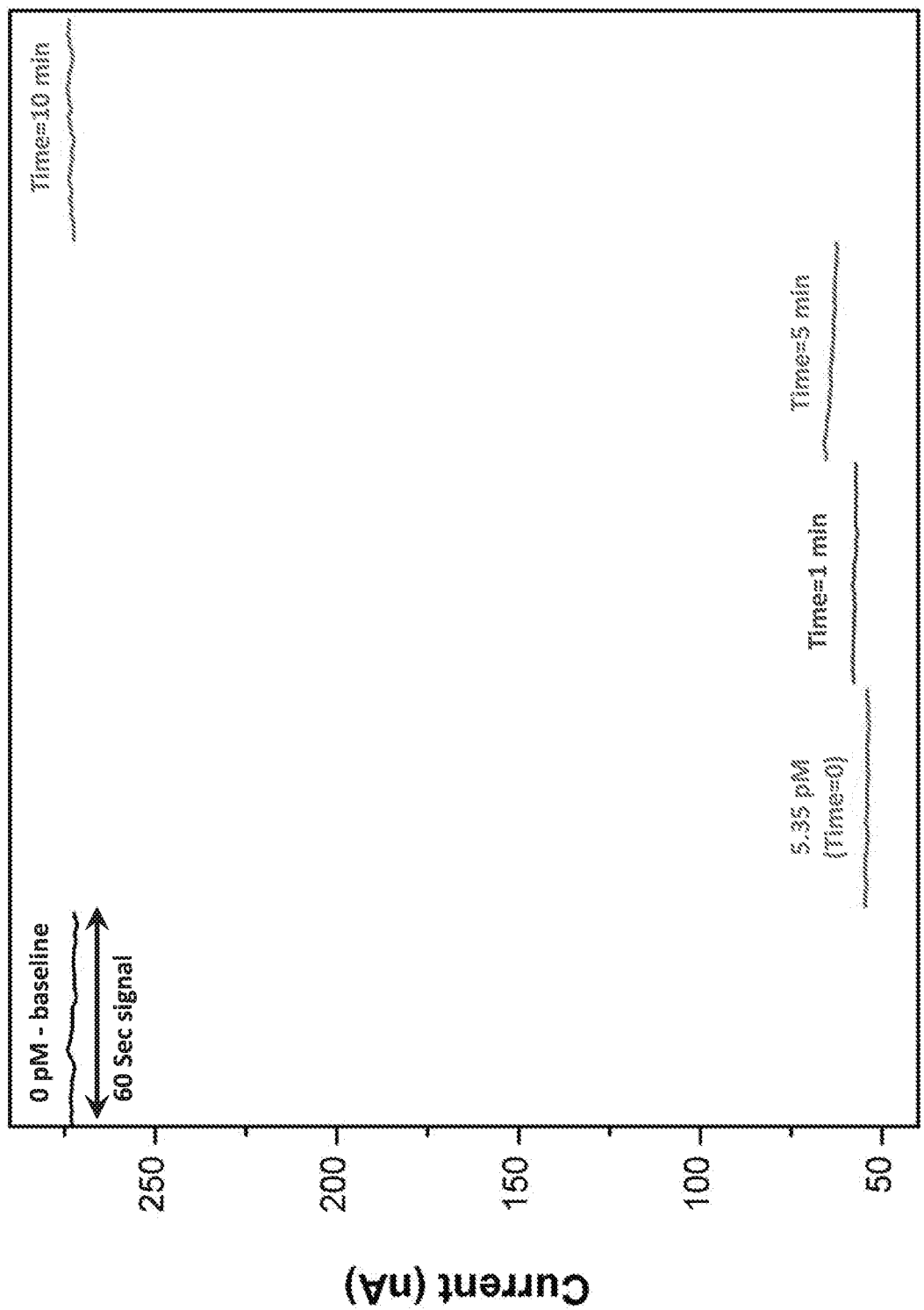

FIG. 6 presents the original signals generated by the modified SiNW forest device during the adsorption of the CA 15-3 solution.

FIGS. 7A-B present the desorption of CA 15-3 from the modified SiNW forest device upon application of light irradiation (HPTS excitation), by percents (%) of the desorbed antigen (FIG. 7A) and by the concentration of the desorbed antigen (FIG. 7B), showing that more than 80% of the adsorbed antigen are released upon 10 minutes of radiation.

Figure 8:
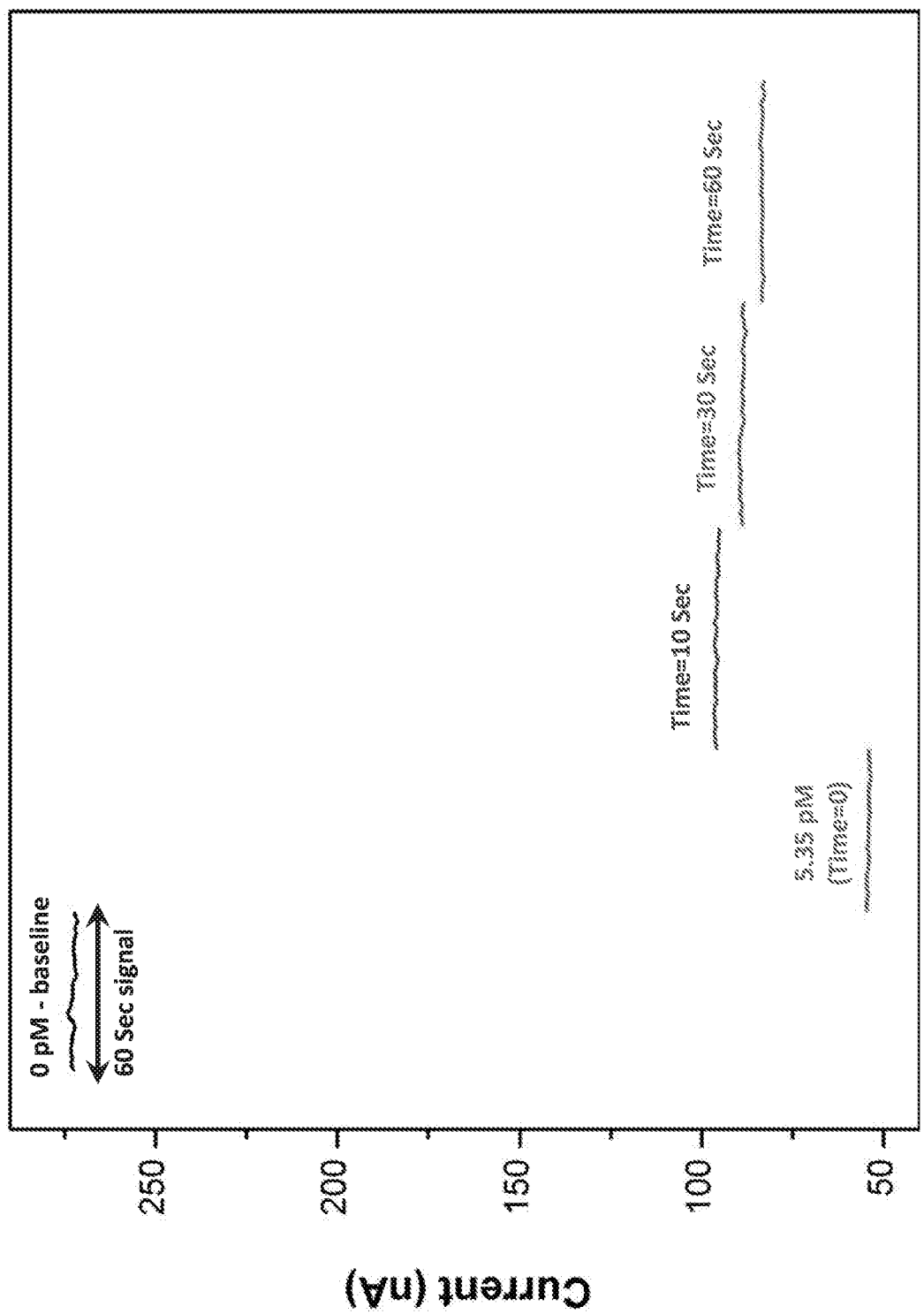

FIG. 8 presents the original signals generated by the modified SiNW forest device during the desorption of the adsorbed CA 15-3 solution.

Figure 9:
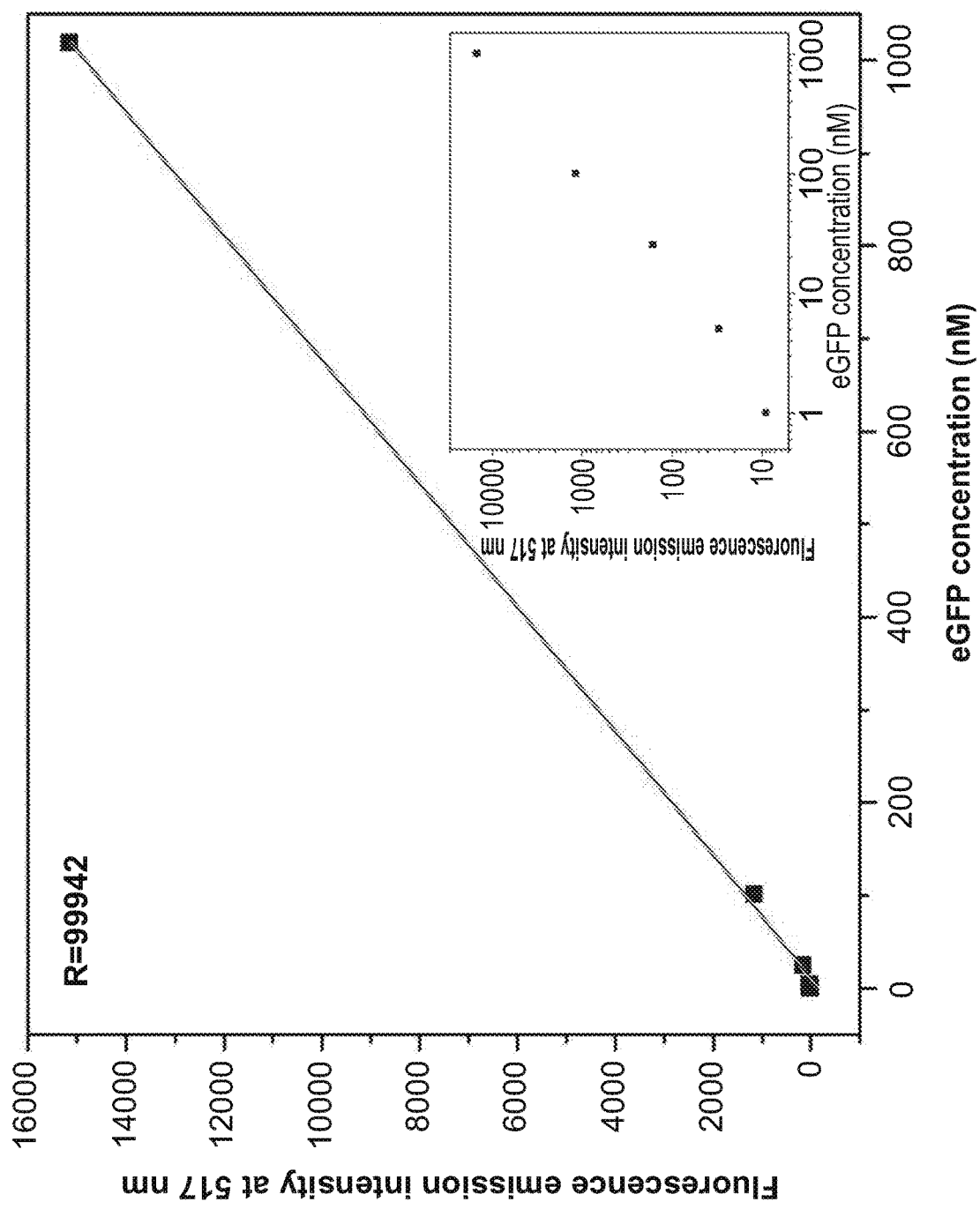

FIG. 9 presents a calibration curve of the fluorescence emission intensity of eGFP as a function of its concentration. Inset shows log-log plot of the calibration curve.

Figure 10:
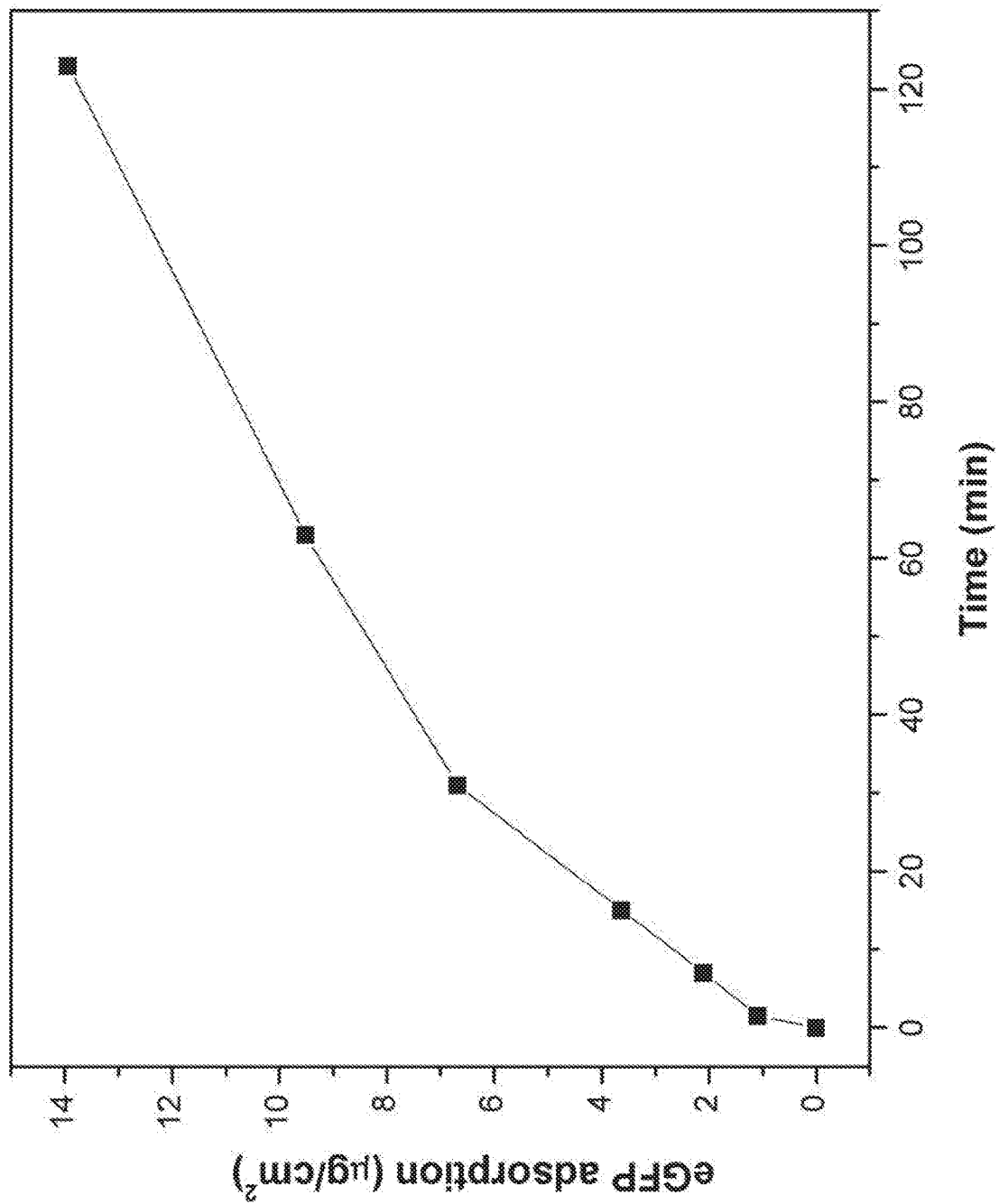

FIG. 10 presents a graph showing adsorption kinetics of eGFP on SiNW forest surface modified with anti-eGFP and HTPS.

Figure 11:
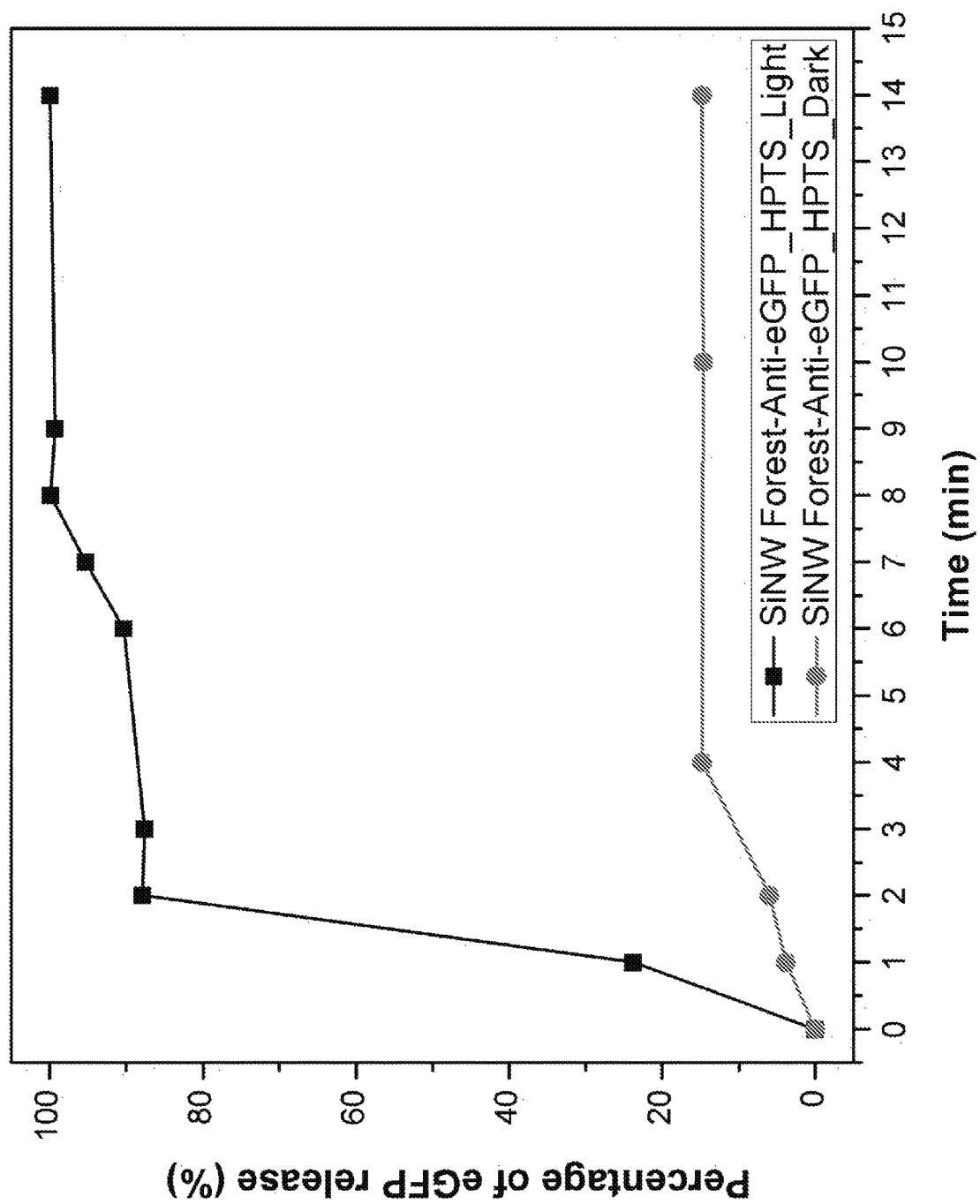

FIG. 11 presents a graph showing the desorption kinetics of the adsorbed eGFP when exposed to light (dark gray squares) and at dark (light gray circles).

Figure 12:
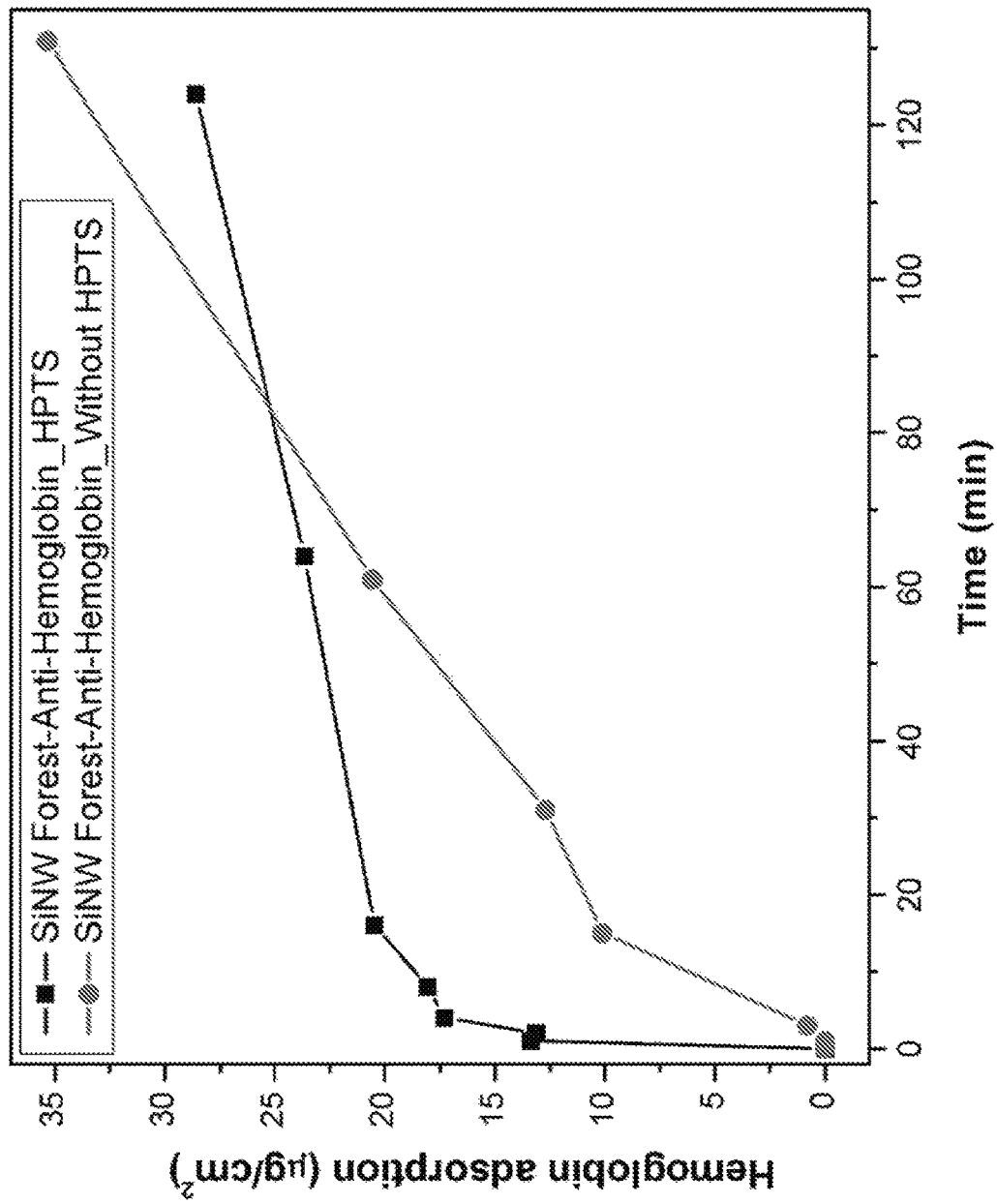

FIG. 12 presents comparative plots showing the adsorption kinetics of hemoglobin to SiNW forest surface modified with anti-hemoglobin (light gray circles) and with anti-hemoglobin and HPTS (dark gray squares).

Figure 13:
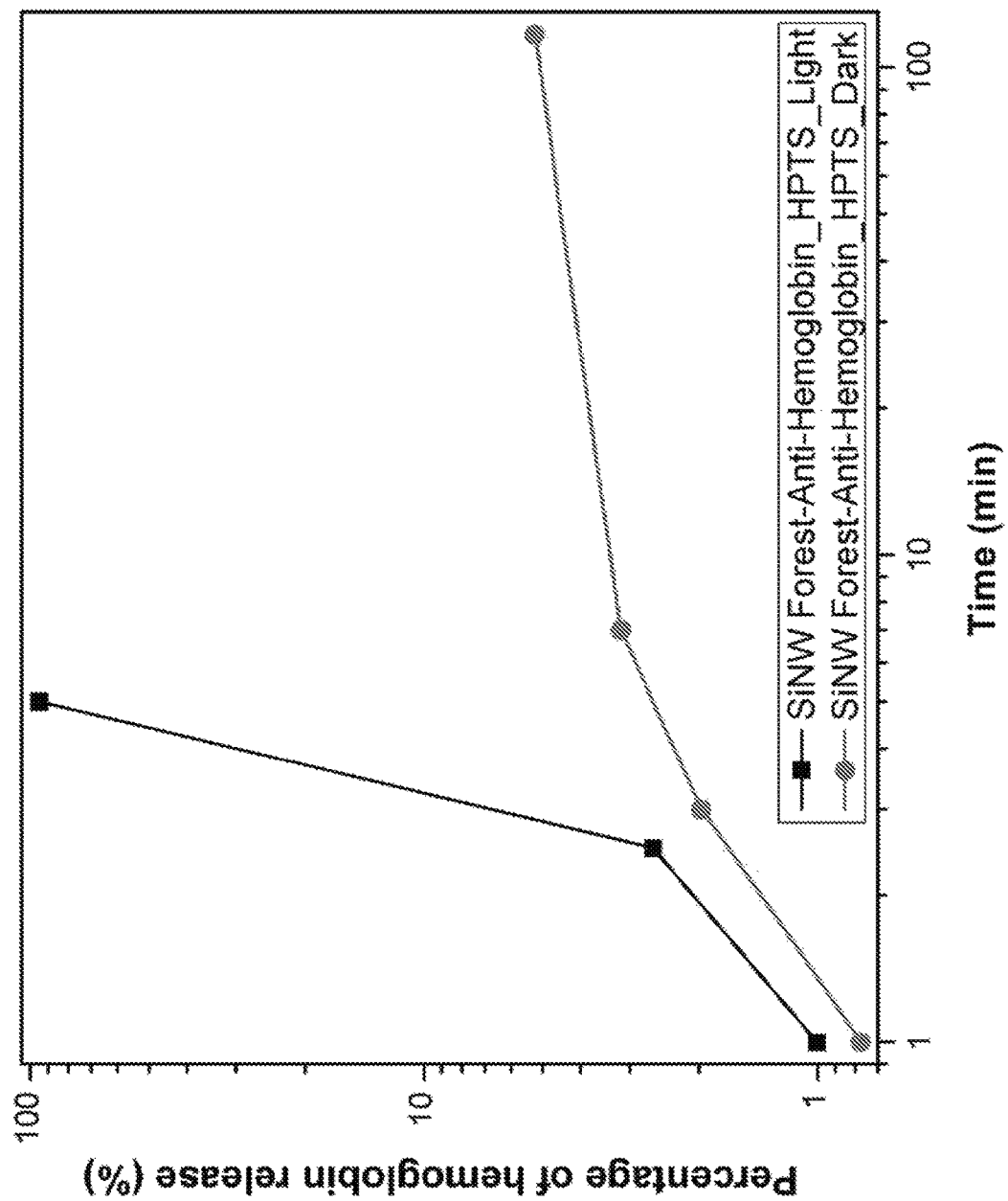

FIG. 13 presents the desorption kinetics of the adsorbed hemoglobin when exposed to light (dark gray squares) and at dark (light gray circles).

Figure 14:
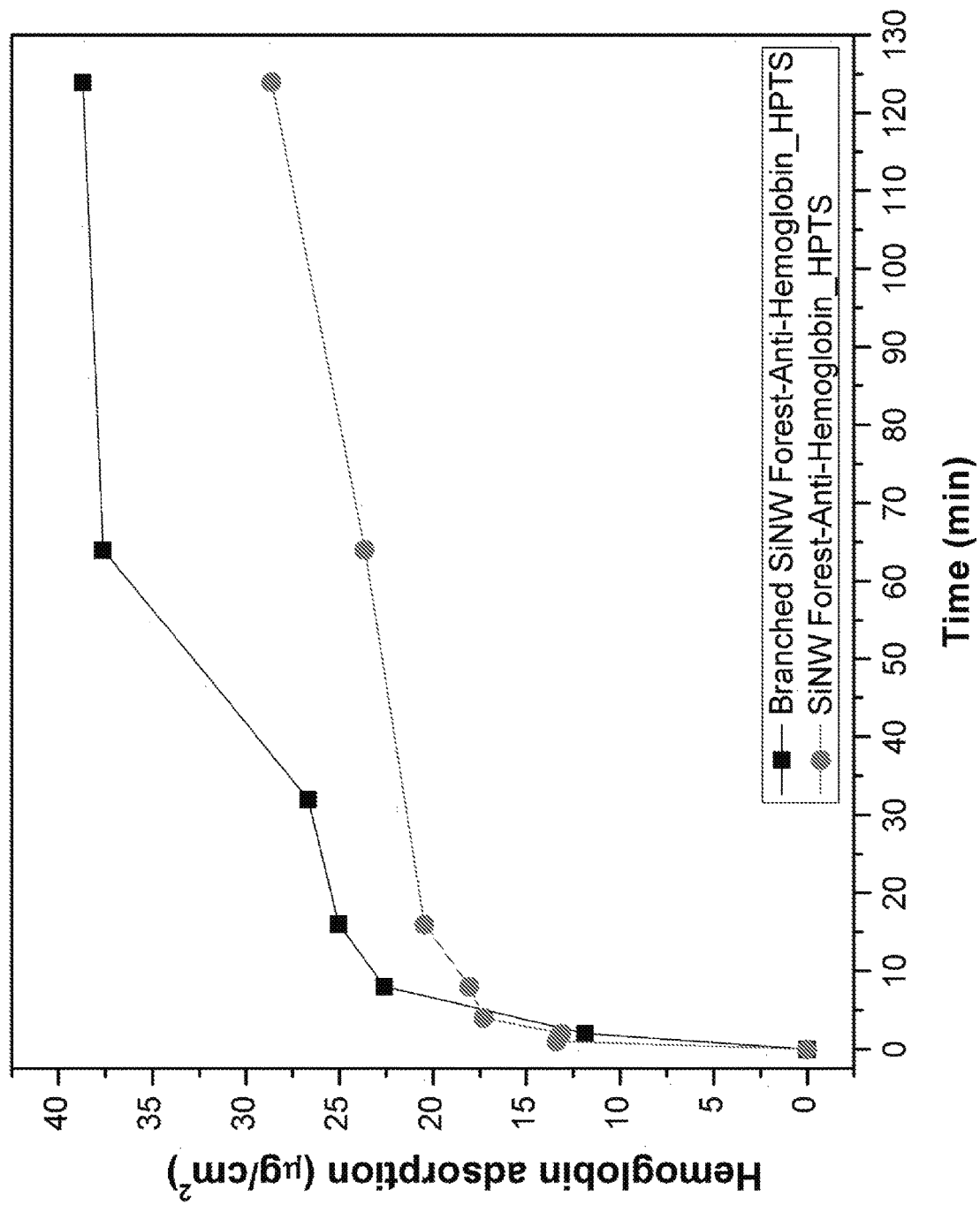

FIG. 14 presents comparative plots showing the improved adsorption of hemoglobin to branched SiNW forest surface modified with anti-hemoglobin and HPTS, compared to similarly modified SiNW forest.

Figure 15:
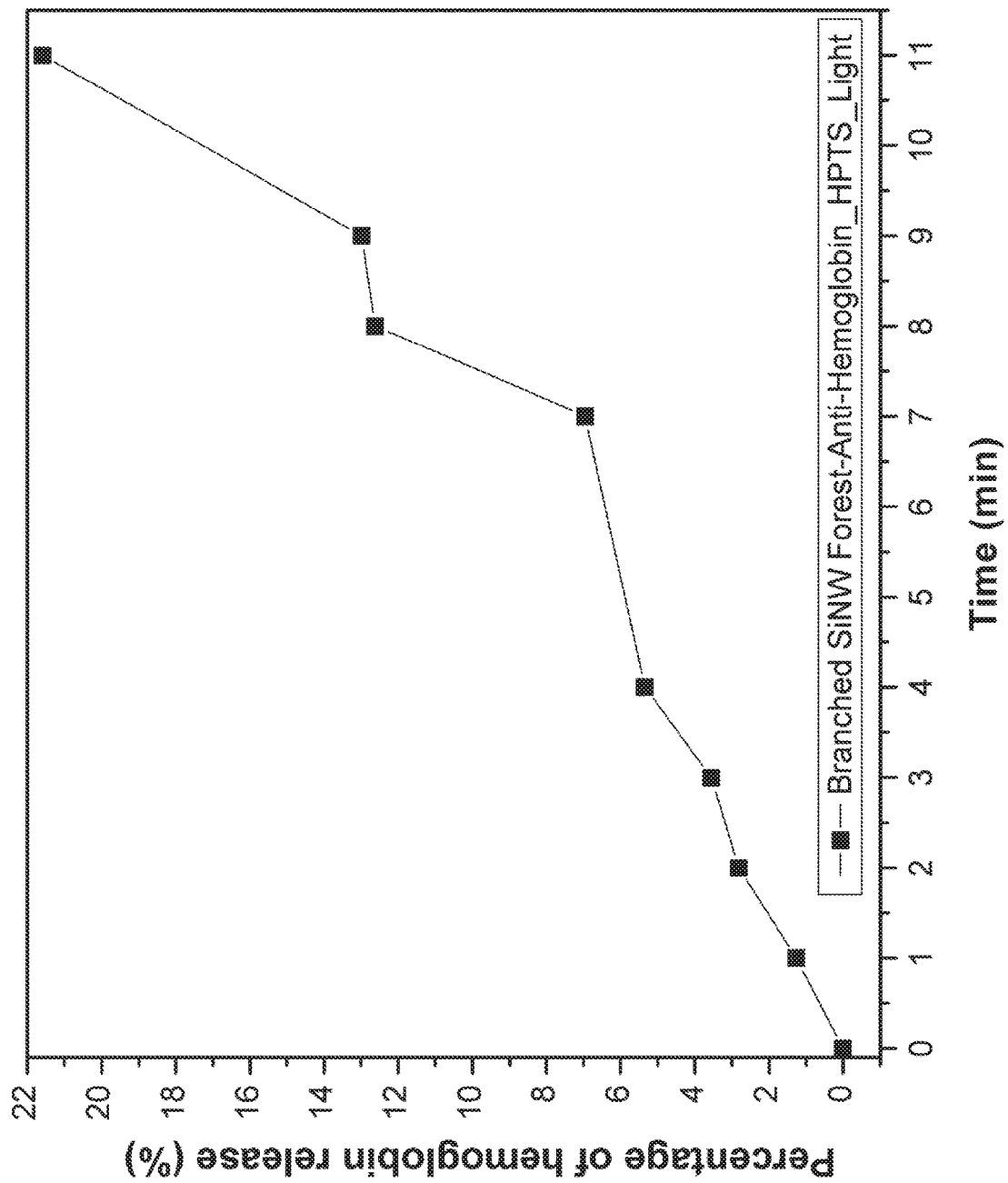

FIG. 15 presents the desorption of the hemoglobin adsorbed to branched SiNW forest when exposed to light.

Figure 16:
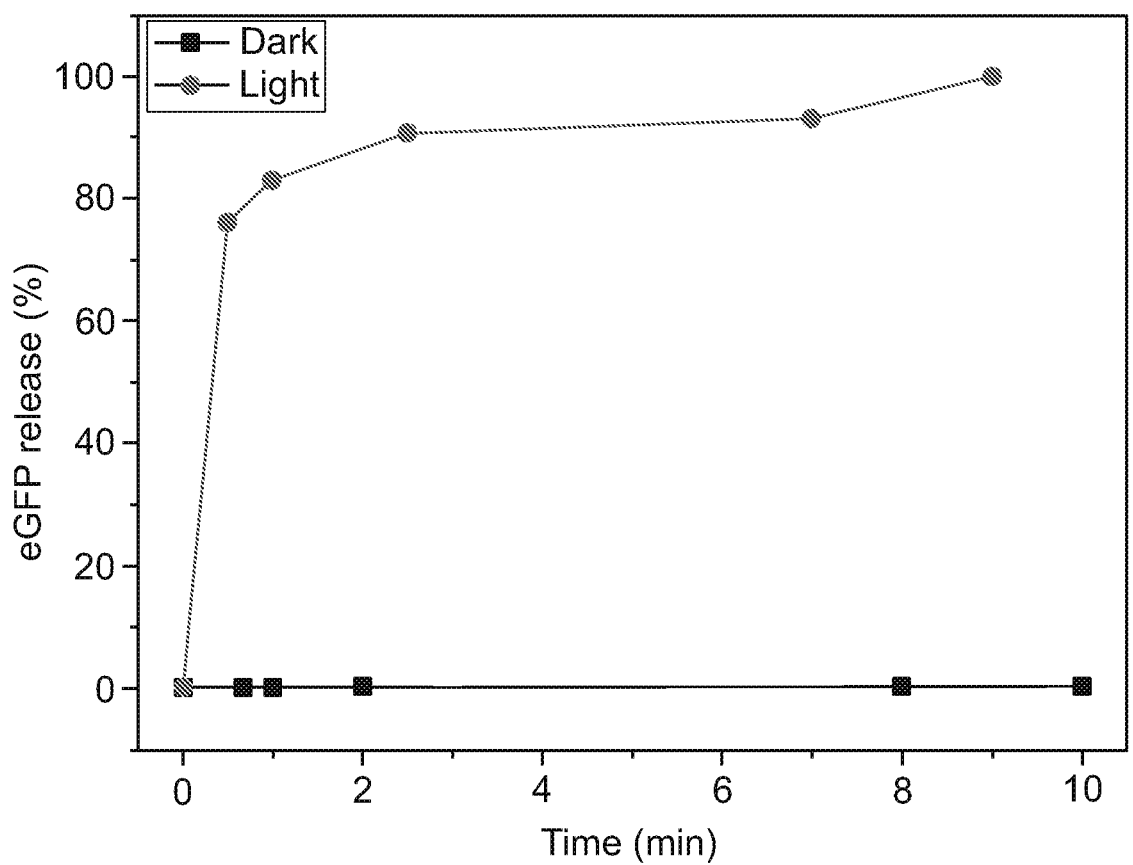

FIG. 16 presents a graph showing the desorption kinetics of eGFP absorbed to SiNW forest surface modified with anti-eGFP and HTPS, upon contacting a blood sample spiked with eGFP with the SiNW forest, when exposed to light (light gray circles) and at dark (dark gray rectangulars).

DESCRIPTION OF SPECIFIC EMBODIMENTS OF THE INVENTION

The present invention, in some embodiments thereof, relates to separation/extraction of analytes, and, more particularly, but not exclusively, to systems usable in, and methods for, selectively separating analytes of interest (e.g., biomolecules such as biomarkers) from a liquid mixture containing same, for example, from a biological sample.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In a search for novel and improved methodologies for selective separation and of analytes from complex liquid mixtures, the present inventors have devised a methodology that utilizes a system having an ultra-large surface area and capability to selective absorb analytes from a liquid sample, and have further devised a methodology that allows fast release of the absorbed analytes from the system.

The system is based on a dense "forest" of nanostructures that have a capturing moiety, that selectively interacts with an analyte, covalently attached to a surface thereof, and of nanostructures that have a light-activatable (photoactivatable) moiety that, upon exposure to light, generate a moiety that interferes with the interaction of the capturing moiety and the analyte, thereby leading to release of the analyte from the system, thus facilitating further determination the analyte (e.g., a level of the analyte in the sample).

Embodiments of the present invention provide a light-controlled system for filtering, selectively separating, desalting, and/or pre-concentrating liquid mixtures and for a controlled release platform, usable in direct analysis of complex liquid mixtures such as whole blood and other complex biosamples.

The system is made of a multiplicity of elongated nanostructures preferably featuring a rough and/or porous surface, modified by a capturing moiety that selectively interacts with an analyte, and by a light-activatable moiety, which, when activated, induces a release of the analyte, thereby allowing a direct extraction and optionally further analysis of analytes from liquid mixtures containing same.

In exemplary embodiments, the separation of analytes-of-interest (e.g., biomarkers) from raw biosamples is performed using a roughness-controlled, optionally branched, silicon nanowire forest of ultra-large binding surface area, modified by a capturing moiety that is selective towards the analyte, followed by the fast release of target proteins in a controlled liquid media, using drastic pH change near silicon nanowire surface. The pH change is caused by illumination of light-activatable moiety (e.g., photo-acid/photo-base) which is covalently bonded to nanowires surface.

A 3D nanostructure system as described herein, in some embodiments, serves as an on-chip filter with ultra-large binding surface area and optionally reversible light-controlled release of adsorbed analyte (marker) molecules for direct purification of e.g., blood samples, is able to selectively collecting and separating specific low abundant biomarkers, while easily removing unwanted blood components (proteins, cells) and achieving desalting effects, without the requirement of time consuming centrifugation steps, and without the use of desalting or affinity columns. The light controlled filter separation system can be easily integrated in a single platform with downstream sensors such as SiNW-based sensor arrays, for the multiplex, real-time and ultrasensitive detection (sensing) of biomarkers.

The methodology disclosed herein provides for the following advantages over currently practiced methodologies: the methodology allows rapid separation while circumventing the need for time consuming processes such as centrifugation, dialysis, affinity columns; the system is label-free, that is, devoid of labeling agents; the system and method can be operated while using very small volume sample; the system is reusable since absorption processes are reversible; the manufacturing and operation are cost-effective; the system is easy to integrate with lab-on-a-chip sensing systems; the system and method are both Multiplex—capable to perform multi-bio-molecular separation; by performing a release of analytes in a controlled liquid media it features desalting capabilities; the light-controlled release of analyte bio-molecules is rapid, within minutes; the methodology performs sample pre-concentration, a feature especially useful for low abundant biomarkers; system and methodology exhibit high selectivity.

The system of the present embodiments can be regarded, and is also referred to herein, as a selective capturing system, or as a selective separation, extraction and/or filtering system, that selectively absorbs (binds) analyte from a liquid mixture comprising same, and can selectively release the absorbed analytes upon illumination. The capturing or separation or filtering system can optionally be in fluid communication with a sensing element or system, which determines a composition, presence and/or level of the released analyte.

Systems and method of the present embodiments can be utilized for fast and direct analyses of various samples, for effecting blood tests, for fast and cheap detection of biomarkers for chronic diseases, and/or as a research tool.

The systems and methods described herein can be easily operated, and can be configured as a lab-on-chip, and thus can be used, for example, at the point of care, without requiring laboratory personnel and/or equipment.

The separation/capturing/filtering system:

According to an aspect of some embodiments of the present invention there is provided a system comprising a substrate and a multiplicity of nanostructures arranged on the substrate at a density of at least 100,000, or at least 200,000, or at least 300,000, or at least 400,000, or at least 500,000, or at least 1,000,000, or at least 2,500,000, or more, nanostructures per 1 $cm^2$.

According to some of any of the embodiments described herein, each nanostructure in at least a first portion of the nanostructures features a capturing moiety covalently attached to a surface thereof and each nanostructure in at least a second portion of the nanostructures features a light-activatable moiety covalently attached to a surface thereof.

Nanostructures Forest:

According to some of any of the embodiments described herein, at least a portion (e.g., at least 50%, or at least 60%, or at least 70%, or at least 80%, or at least 90%, or at least 95%, or at least 99%), and preferably all, of the nanostructures are elongated nanostructures.

As used herein, an "elongated nanostructure" generally refers to a three-dimensional body which is made of a solid substance, and which, at any point along its length, has at least one cross-sectional dimension and, in some embodiments, two orthogonal cross-sectional dimensions less than 1 micron, or less than 500 nanometers, or less than 200 nanometers, or less than 150 nanometers, or less than 100 nanometers, or even less than 70, less than 50 nanometers, less than 20 nanometers, less than 10 nanometers, or less than 5 nanometers. The cross-section of the elongated nanostructure may have any arbitrary shape, including, but not limited to, circular, square, rectangular, elliptical, star-shape and tubular. Regular and irregular shapes are included.

In some embodiments of the present invention, the nanostructure is shaped as a hollow tube, preferably entirely hollow along its longitudinal axis, which is also referred to as "nanotube" or as "nanotubular structure".

The nanotubes can be single-walled nanotubes, multi-walled nanotubes or a combination thereof.

In some embodiments, an average inner diameter of a nanotube ranges from 0.5 nanometers to 200 nanometers, or from 1 nm to 100 nm, or from 1 nm to 50 nm.

In case of multi-walled nanotubes, in some embodiments, an interval distance can range from 0.5 nanometers to 200 nanometers, or from 1 nm to 100 nm, or from 1 nm to 50 nm.

In some of any of the embodiments described herein, an average length of the nanostructures ranges from 0.1 to 500 microns or from 1 to 200 microns, including any intermediate subranges and values therebetween.

In some of any of the embodiments described herein, an average diameter of the nanostructures ranges from 10 nm to 30 microns, including any intermediate subranges and values therebetween.

In some of any of the embodiments described herein, the elongated nanostructures are generally parallel to each other.

In some of any of the embodiments described herein, the elongated nanostructures are aligned generally vertically to the substrate.

In some of any of the embodiments described herein, the elongated nanostructures are generally parallel to each other and are aligned generally vertically to the substrate.

In some of any of the embodiments described herein, an average inter-distance between the nanostructures ranges from 10 nm to 10000 nm, or from 10 nm to 6000 nm, or from 10 nm to 5000 nm, including any subranges and intermediate values therebetween.

The elongated nanostructures of the present embodiments, whether hollowed (tubular) or not, are collectively referred to herein as "nanopillars" or as "nanowires".

Selection of suitable materials for forming a nanostructure as described herein will be apparent and readily reproducible by those of ordinary skill in the art, in view of the guidelines provided herein for beneficially practicing embodiments of the invention.

In some embodiments, the nanostructure of the present embodiments is made of, for example, an element of Group IV, and various combinations of two or more elements from any of Groups II, III, IV, V and VI of the periodic table of the elements.

As used herein, the term "Group" is given its usual definition as understood by one of ordinary skill in the art. For instance, Group III elements include B, Al, Ga, In and Tl; Group IV elements include C, Si, Ge, Sn and Pb; Group V elements include N, P, As, Sb and Bi; and Group VI elements include O, S, Se, Te and Po.

In some embodiments, the nanostructure is a carbon nanostructure, for example, a carbon nanotube.

In some embodiments of the present invention the nanostructure is made of a (e.g., semiconductor) material that is doped with donor atoms, known as "dopant". The present embodiments contemplate doping to effect both n-type (an excess of electrons than what completes a lattice structure lattice structure) and p-type (a deficit of electrons than what completes a lattice structure) doping. The extra electrons in the n-type material or the holes (deficit of electrons) left in the p-type material serve as negative and positive charge carriers, respectively. Donor atoms suitable as p-type dopants and as n-type dopants are known in the art.

For example, the nanostructure can be made from silicon doped with, e.g., B (typically, but not necessarily Diborane), Ga or Al, to provide a p-type semiconductor nanostructure, or with P (typically, but not necessarily Phosphine), As or Sb or to provide an n-type semiconductor nanostructure.

In some of any of the embodiments described herein, the nanostructures comprise silicon. In some of these embodiments, the silicon is doped (e.g., comprises p-type or n-type dopant(s)).

Nanowires or nanopillars comprising silicon are also referred to herein as SiNWs.

A system comprising SiNWs at a configuration as described herein (e.g., at a density as described herein) is also referred to as SiNW forest, or SiNWF.

In some embodiments, at least a portion of the nanostructures comprises nanostructures that feature a rough and/or porous surface. In some of these embodiments, the nanostructure's surface is characterized by a mean roughness height, as determined by atomic force microscopy, transmission electron microscopy or scanning electron microscope according to well know procedures, of from about 1 to about 200 nm, including any intermediate subranges and values therebetween.

Any method for forming a nanostructure and of constructing an array of a plurality of nanostructures as described herein is contemplated.

In some embodiments, the nanostructures are formed by etching, that is, subtracting a bulk made of the nanostructures' material, using a mask, to thereby obtain the desired configuration. In some embodiments, the mask is in a form of beads, and the beads' average diameter and shape determine the diameter and roughness, respectively, of the nanostructures. In some embodiments, the roughness of the beads is manipulated prior to the etching, so as to obtain a desired roughness of the nanostructures.

In some embodiments, the beads are polystyrene beads, and in some embodiments, the polystyrene beads are etched so as to feature irregular shape that provides nanostructures exhibiting a roughness as described herein.

In some embodiments, the etching is wet etching.

The etching reagents and conditions are selected according to the material to be etched and the mask, so as to selectively etch the bulk material. Selecting the etching reagents and conditions can be readily performed by those skilled in the art.

An exemplary method of preparing SiNW forest according to the present embodiments is described in Example 1 of the Examples section that follows.

An exemplary method of preparing SiNW forest according to the present embodiments is described in Krivitsky et al., Nano letters 2012 (supra).

Nanostructures Branched Forset:

In a search for a system with larger surface area and capturing capabilities, the present inventors have devised a novel system, which comprises branched nanostructures. The present inventors have conceived that due to the capability to readily release the captured analytes, which is enabled by the design of the present embodiments (the co-inclusion of a light-activatable moiety), nanostructures featuring a further enlarged surface area can still be used for separation and subsequent release of the analytes, without adversely affecting the release profile of the analyte by the more complex nanostructures network.

While reducing these embodiments to practice, the present inventors indeed demonstrated a capability to absorb and readily desorb analytes from liquid mixtures using such a system.

In some of any of the embodiments described herein, at least a portion of the nanostructures in a separation/filtering system as described herein in any of the respective embodiments are branched nanostructures.

According to an aspect of some embodiments of the present invention there is provided a system comprising a substrate and a multiplicity of nanostructures arranged on the substrate as described herein (e.g., aligned generally vertically to the substrate; and/or being generally perpendicular to one another) at a density of at least 100,000, or at least 200,000, or at least 300,000, or at least 400,000, or at least 500,000, or at least 1,000,000, or at least 2,500,000, or more, nanostructures per 1 $cm^2$, as described herein in any of the respective embodiments, at least a portion of the nanostructures being branched nanostructures.

By "branched nanostructure" it is meant a nanostructure that has tree-like shape, such that a nanostructure as described herein in any of the respective embodiments is a main axis, similarly to a tree stem, and is referred to herein as the "main nanostructure" and nanostructure branches are extending from the main axis. Each such nanostructure branch can further be branched, by having nanostructure branches extending therefrom.

In some of any of the embodiments described herein for branched nanostructures, each main nanostructure in branched into 10-100,000 branches, and each of these branches can individually be further branched into 10-100,000 branches. Each nanostructure can therefore feature from 10 to 1,500,000 branches.

In some embodiments, the nanostructure branches are as described herein for the main nanostructure in any of the respective embodiments and any combination thereof.

In some embodiments, the main nanostructure and the nanostructure branches are made of the same material, and in some embodiments, from different materials.

In some embodiments, the nanostructure branches feature shape, roughness and/or dimensions identical or similar to the main nanostructure, and in some embodiments, the branches feature different shape, roughness and/or dimensions.

In some of any of the embodiments described herein for branched nanostructures, an average length of each branch independently ranges from 5 to 40000 nm, including any intermediate values and subranges therebetween.

In some of any of the embodiments described herein for branched nanostructures, an average diameter of the nanostructure branches independently ranges from 2 to 200 nm, including any intermediate values and subranges therebetween.

In some of any of the embodiments described herein, the nanostructure branches are non-hollowed (non-tubular) elongated nanostructures.

In some of any of the embodiments described herein for branched nanostructures, the nanostructure branches are entangled with one another, that is, branches of one nanostructure are entangled with branches of another nanostructure and/or branches of different nanostructure branches of the same main nanostructure are entangled with one another.

In some embodiments, the entangled branched nanostructures form a dense three-dimensional network. An exemplary such 3D network is depicted in FIGS. 4A-D.

In some of any of the embodiments described herein, the nanostructure branches comprise silicon, as described herein for any of the respective embodiments of a nanostructure.

A system according to these embodiments is also referred to herein as a branched nanostructure forest, a branched forest, for example, a branched SiNW forest, or BSiNWF.

A branched nanostructure forest as described herein can be made by methodologies known in the art for constructing an array of a plurality of branched nanostructures.

In some embodiments, the main nanostructures are formed by means of wet etching, as described herein, and the branches are grown from the main nanostructures using, for example, chemical vapor deposition. Alternatively, the nanostructure branches can be made using laser assisted catalytic growth (LCG). In some embodiments, the nanostructure branches are grown from the main nanostructures using methodologies as described, for example, in WO 2015/059704, WO 2017/098517 and WO 2018/037406

An exemplary method is described in Example 2 in the Examples section that follows.

In some of any of the embodiments described herein for a branched nanostructure forest, a capturing moiety that selectively interacts with an analyte, as described herein, is covalently attached to at least a portion of the nanostructure branches.

In some of any of the embodiments described herein for a branched nanostructure forest, a light-activatable moiety as described herein is covalently attached to at least a portion of the nanostructure branches.

In some of any of the embodiments described herein for a branched nanostructure forest, a capturing moiety and a light-activatable moiety as described herein are both covalently attached to a nanostructure branch in at least a portion of the nanostructure branches.

Analyte, Capturing Moiety and the Light-Activatable Moiety:

According to some of any of the embodiments described herein, at least a first portion of the nanostructures or nanostructure branches has a capturing moiety covalently attached to a surface thereof and at least a second portion of the nanostructures or nanostructure branches has a light-activatable moiety covalently attached to a surface thereof.

In some embodiments, the first and second portions are the same, such that at least a portion of the nanostructures or the nanostructure branches have both a capturing moiety and a light-activatable moiety attached to a surface thereof.

In some embodiments, at least one, preferably at least a portion, and more preferably at least 50%, or at least 60%, or at least 70%, or at least 80%, or more, of the nanostructures or nanostructure branches has both the capturing moiety and the light-activatable moiety covalently attached to a surface thereof.

In some embodiments, the first and second portions are different, such that some the nanostructures or the nanostructure branches have a capturing moiety but not a light-activatable moiety attached to a surface thereof and other nanostructures or nanostructure branches have a light-activatable moiety but not a capturing moiety attached to a surface thereof. In some of these embodiments, at least some of the nanostructures or nanostructure branches that have a light-activatable moiety attached thereto are in proximity to nanostructure or nanostructure branches that have a capturing moiety attached thereto.

In some of any of the embodiments described herein, a total amount of the capturing moiety or moieties in the system ranges from about 1 ng/cm$^2$ to about 1 mg/cm$^2$, or from about 100 ng/cm$^2$ to about 800 µg/cm$^2$, or from about 10 µg/cm$^2$ to about 800 µg/cm$^2$, or from about 10 µg/cm$^2$ to about 300 µg/cm$^2$, including any intermediate values and subranges therebetween. In exemplary embodiments, each capturing moiety is in an amount of about 30 µg/cm$^2$ in the system.

The Analyte and Capturing Moiety:

The capturing moiety according to the present embodiments is such that selectively interacts with an analyte of interest, as described herein.

Herein throughout, the term "analyte" is also referred to interchangeably as "target analyte" or "target molecule", and encompasses chemical and biological species, including small molecules and biomolecules such as, but not limited to, peptides, proteins, nucleotides, oligonucleotides, and polynucleotides.

In some embodiments, the sample is a biological sample, as described herein, and the analyte is a bioanalyte, that is, a chemical or biological species that is present in biological systems, for example, a biological system of a subject, as defined herein.

Alternatively, the analyte is a marker that is indicative of presence or level of hazardous materials in a liquid, such as, but not limited to, water pollutants, chemical agents, biological organisms or radiological conditions in water, including groundwater, or in liquid waste.

In some embodiments, the bioanalyte is a biomarker.

The term "biomarker" describes a chemical or biological species which is indicative of a presence and/or severity of a disease or disorder (a medical condition) in a subject. Exemplary biomarkers include small molecules such as metabolites, and biomolecules such as antigens, hormones, receptors, and any other proteins, as well as polynucleotides. Any other species indicative of a presence and/or severity of a medical condition is contemplated.

The interaction between the capturing moiety and the analyte typically involves binding, and may further involve activation and/or chemical interaction such as chemical reaction.

By "selectively interacts" it is meant that the capturing moiety binds to the analyte at a much higher level than to another, even structurally or functionally similar, species.

In some embodiments, the capturing moiety is such that a has binding affinity with the analyte that is characterized by a dissociation constant, Kd or $K_D$, of no more than 1 mM, or no more than 100 nM, or no more than 10 nM, or no more than 1 nM, or no more than $10^{-10}$M, or no more than $10^{-12}$M, and even lower, e.g., as low as $10^{-15}$M.

Herein and in the art, a dissociation constant, $K_D$ represents: $[A]\times[B]/[AB]$, wherein A is a first member of a pair, and B is a second member of pair.

The interaction between the capturing moiety and the analyte can be reversible or irreversible, and is preferably reversible.

In some embodiments, the capturing moiety selectively interacts with the analyte as defined herein, but not with background components in the liquid sample. Such background components can include other biomolecules, as described herein, salts, and other chemical and biological species.

In some of any of the embodiments described herein, the analyte and the capturing moiety form an affinity pair, as defined herein.

In some embodiments, the analyte is a bioanalyte, e.g., a biomarker, as described herein, and the capturing moiety is an analyte specific reagent, as defined by the FDA (see, (ASRs) in 21 CFR 864.4020).

In some embodiments, the bioanalyte and the capturing moiety form an affinity pair, characterized by a dissociation constant, $K_D$ as described herein.

Exemplary affinity pairs include, without limitation, an enzyme-substrate pair, a polypeptide-polypeptide pair (e.g., a hormone and receptor, a ligand and receptor, an antibody and an antigen, two chains of a multimeric protein), a polypeptide-small molecule pair (e.g., avidin or streptavidin with biotin, enzyme-substrate), a polynucleotide and its cognate polynucleotide such as two polynucleotides forming a double strand (e.g., DNA-DNA, DNA-RNA, RNA-DNA), a polypeptide-polynucleotide pair (e.g., a complex formed of a polypeptide and a DNA or RNA e.g., aptamer or of complementary peptide nucleic acid and oligonucleotide), a polypeptide-metal pair (e.g., a protein chelator and a metal ion), a polypeptide and a carbohydrate (leptin-carbohydrate), and the like.

In the context of the present embodiments, one member of an affinity pair is an analyte and the other is the capturing moiety.

In some embodiments, the analyte is a protein biomarker, for example, a receptor or an antigen, and the capturing moiety is a ligand of the protein, for example, a receptor ligand or an antibody, respectively.

In some embodiments, the analyte is an antigen and the capturing moiety is an antibody or a fragment thereof having a high affinity, as defined herein, to the antigen.

In some embodiments, the analyte (also referred to herein as "analyte of interest") is a marker, that is, a molecule that is indicative of a condition, for example, a medical condition.

In some embodiments, the analyte is a biomolecule, and in some embodiments, it is a biomarker.

Exemplary biological affinity pairs include, but are not limited to, an antigen-antibody pair, a receptor-ligand pair, an enzyme-substrate pair, a streptavidin-biotin pair, a protein-cofactor pair, a protein-protein pair, and pairs of complementary oligonucleotides (e.g., DNA-DNA; DNA-RNA, RNA-RAN), or of oligonucleotide-peptide nucleic acid.

According to some embodiments of the invention, the capturing moiety comprises an immunogenic moiety. According to some embodiments of the invention, the immunogenic moiety comprises an antibody or a fragment thereof. According to some embodiments of the invention, the immunogenic moiety comprises an antigen. In these embodiments, the marker is a biomarker that preferably comprises an antibody to the antigen. Alternatively, the marker is a biomarker that preferably comprises an antigen and the capturing moiety comprises an antibody to the antigen. According to some embodiments of the invention, the capturing moiety comprises a ligand. In these embodiments, the marker is preferably a biomarker that comprises a receptor.

The capturing moiety can be attached to the surface of the nanostructure or nanostructure branch by any technique known in the art, such as, but not limited to, the technique that is based on fragmentation of antibody-capturing units and that is described in Elnathan et al., Nano Lett 2012, 12, (10), 5245-5254, the contents of which are hereby incorporated by reference.

In some embodiments, the capturing moiety is an antibody and the analyte is a biomolecule that selectively interacts with the antibody.

In some embodiments, the analyte (marker or biomarker) is an antigen.

In some of any of the embodiments described herein, the capturing moiety and the analyte feature a pH-dependent dissociation constant.

By "pH-dependent dissociation constant" it is meant that the dissociation constant $K_D$, as defined herein, increases by at least one order of magnitude, preferably by 2 or more orders of magnitude, as a result of a change in the pH of the surrounding environment of one pH unit. For example, a pair of a capturing moiety and an analyte that has $K_D$ of $10^{-10}$ M at pH=7, feature $K_D$ of $10^{-1}$ M at pH=2. As another example, a pair of a capturing moiety and an analyte that has $K_D$ of $10^{-10}$ M at pH=7, feature $K_D$ of $10^{-1}$ M at pH=12.

The capturing moiety can be attached to the surface of the nanostructure or nanostructure branch by means of reactive groups within the capturing moiety and compatible reactive groups on the surface of the nanostructure or the nanostructure branch, directly or via a linker. Preferably, the attachment is a covalent attachment. In exemplary embodiments, the linker generates a reactive amine group on the surface of the nanostructure or nanostructure branch, which is optionally subjected to reductive amination to provide an aldehyde-terminated surface group that binds to an amine group of the capturing moiety.

The reactive groups on the surface of the nanostructure or nanostructure branch can be intrinsic or can be generated upon a treatment.

In some embodiments, when the nanostructure is SiNW or silicon nanotubes, free hydroxyl groups are intrinsically present on the surface of the nanostructures and can be utilized for attaching functional moieties thereto.

Alternatively, the nanostructures described herein are first surface-modified so as to generate surface reactive groups. Such a surface modification can be performed by, for example, surface treatment such plasma treatment, which exposes surface reactive groups, and/or by attaching to thus exposed or to intrinsic functional groups on the nanostructure surface a bifunctional linker molecule, which comprises in one terminus thereof a reactive group that is capable of forming a bond with these intrinsic functional groups and in another terminus thereof a reactive group that can covalently attach to the capturing moiety.

In some embodiments, the capturing moiety is attached to the nanostructure via a bifunctional linker, as described herein.

An exemplary such a linker is derived from a silyl that comprises 1, 2 or 3-living groups that allows the silyl to interact with intrinsic hydroxyl groups on the silicon nanostructure surface, forming —Si—O—Si bonds, and 1, 2 or 3 hydrocarbon groups (e.g., alkyl, alkylene, cycloalkyl, aryl) terminating with a reactive group that is capable of covalently attaching to the capturing moiety.

Alternatively, the linker can be derived from an orthosilicate that comprises 1, 2, or 3 OR' groups, with can interact with intrinsic hydroxyl groups on the silicon nanostructure surface, forming —Si—O—Si bonds, and 1, 2 or 3 hydrocarbon groups (e.g., alkyl, alkylene, cycloalkyl, aryl) terminating with a reactive group that is capable of covalently attaching to the capturing moiety.

In some of these embodiments, the hydrocarbon is alkyl, for example, of 1-10, or of 1-6 carbon atoms. An exemplary alkyl is propyl. Other alkyls, for example, ethyl, butyl, pentyl, and hexyl, and higher alkyls are also contemplated.

In exemplary embodiments, the linker generates amine surface reactive groups, which are further reacted with a dialdehyde, to thereby generate an aldehyde surface group that can react with capturing moieties featuring an amine group, to thereby form an imine bond.

The light-activatable moiety:

The light-activatable moiety is such that generates, upon exposure to light, a light-activated, reactive moiety that interferes with an interaction of the capturing moiety and the analyte of interest.

In some embodiments, activating the light-activatable moiety comprises exposing the system to light at a wavelength that generates the light-activated reactive moiety that interferes with the interaction.

The light-activatable moiety can be activated and thereby interfere with the interaction of the capturing moiety and the analyte by exposure to light at any wavelength, preferably within the UV-vis range.

In some embodiments, the light-activatable moiety is such that induces conditions that interfere with the interaction between the capturing moiety and the analyte (e.g., result in increasing the $K_D$ of the capturing moiety and the analyte) upon being exposed to light.

In some embodiments, the light-activated, reactive moiety, formed upon exposing the light-activatable moiety to light, is such that induces a release of at least 20% of analyte molecules that interact with the capturing moieties in 10 minutes.

A light-activatable moiety as described herein is also referred to herein and in the art as "photoactivatable moiety", and describes a chemical moiety that has light-absorbing characteristics, and which, as a result of light absorbance, undergoes a chemical change. The chemical change can be, for example, a change in a configuration (e.g., stereoconfiguration, isomerization) and/or a change that results in a release of a chemical moiety and/or a generation of a chemical moiety that is different from the light-activatable moiety before illuminated (e.g., ring closure, ring opening).

The light activatable moiety can induce the above-mentioned conditions, upon exposure to light, by generating a reactive moiety, which is also referred to herein as "light-activated moiety", since it is generated upon activation by light.

The reactive moiety can be generated, upon exposure to light, by a change in the configuration of the light-activatable moiety and/or upon a release of a chemical moiety, as described herein.

In some embodiments, the light activated moiety provides, near the nanostructure's surface, conditions which promote dissociation of the capturing moiety and the analyte, when interacted with one another, and thereby interferes with the interaction of the capturing moiety and the analyte.

In some of any of the embodiments described herein, the light-activatable moiety induces, upon exposure to light, a change in the pH in the environment of the capturing moiety. In some of these embodiments, the capturing moiety and the analyte feature a pH-dependent dissociation constant, as defined herein, and the change in the pH results in increasing the dissociation constant, and thereby to the release of the analyte.

Light-activatable moieties that induce a change in pH of their environment are known in the art and encompass photoacids and photobases.

Photoacids are molecules which become more acidic, and capable of releasing protons, upon absorption of light. The release of protons may result either due to a generation of a strong acid upon a light-induced dissociation of a chemical moiety or group (in which case the light-activated, reactive group in the strong acid), or due to a light-induced dissociation of protons upon photoassociation (e.g. ring-closing), in which case the light-activated, reactive group comprises protons.

When the reactive moiety comprises protons dissociated from the photoacid upon exposure to light, the dissociation can be either irreversible or reversible. Photoacids that result in irreversible dissociation of protons are also referred to in the art as photoacid generators. Photoacids that results in reversible dissociation of protons are also referred to in the art as photoacids.

In some of any of the embodiments described herein, the light-activatable moiety is a moiety derived from a photoacid. An exemplary photoacid is the fluorescent dye pyranine (8-hydroxy-1,3,6-pyrenetrisulfonate or HPTS).

Exemplary photoacid generators are compounds, or moieties derived therefrom, which include a triphenylsulfonium triflate.

Photobases are molecules which become more basic, and capable of releasing base molecules or to conjugate protons upon exposure to light. The base molecules can be, for example, amines, hydroxides, sulfoxides, slufonates, sulfonamides, etc.

Exemplary photobases include benzyl carbamates, benzoin carbamates, carabmoyloximes, aromatic sulfonamides, and like amine-generating photobases.

In some of these embodiments, the light-activatable moiety generates, upon the exposure to light, a reactive moiety that increases proton concentration near the nanostructure's surface (a photo-acid), or a moiety that reduces proton concentration near the nanostructure's surface (a photo-base), thereby promoting the pH-dependent dissociation of the capturing moiety and the analyte, as required or desired.

The attachment of a light-activatable moiety to the nanostructure or nanostructure branches can be performed as described herein for attaching a capturing moiety, while covalently attaching a light-activatable compound (e.g., a photoacid or a photobase) via chemical groups thereof to surface groups of the nanostructure or nanostructure branches, directly or via a linker, as described herein, without affecting its capability to absorb light and to generate a reactive moiety and/or conditions that affect the dissociation of the analyte from the capturing moiety.

In some of any of the embodiments described herein, the light-activatable moiety is selected in accordance with the conditions desired to interfere with the interaction of the capturing moiety and the analyte (e.g., a pH at which the dissociation constant is high).

Exemplary Configurations:

Referring now to the drawings, FIG. 1 illustrates an exemplary system according to some embodiments of the present invention, featuring silicon nanowires having covalently attached thereto (immobilized thereto) an antibody, and a photo-acid/photo-base light activatable moiety. As shown therein, upon illumination, the light-activatable moiety is excited to produce a light-activated moiety that induces pH change near the nanowires surface, and promotes dissociation between the analyte (an antigen) and the antibody.

In some embodiments, the nanostructures or nanostructure branches have covalently attached to their surface two or more capturing moieties, each selectively interacts with a different analyte.

When two or more capturing moieties are attached, each can be attached to a different portion of the nanostructures or nanostructure branches, or, both can be attached to the same nanostructures or nanostructure branches.

In some embodiments, the nanostructures have covalently attached to their surface two or more light-activatable moieties, each providing a different light-activated moiety, and, in some embodiments, each of the light-activated moieties interferes with the interaction between different capturing moiety-analyte pairs. Alternatively, or in addition, each light-activatable moiety generates a light-activated moiety upon exposure to light at different wavelength, such that at each wavelength, interference with the interaction of a different pair of capturing moiety-analyte occurs, thereby selectively controlling the release of the analyte from the system.

When two or more capturing moieties are attached, each can be attached to a different portion of the nanostructures or nanostructure branches, or, both can be attached to the same nanostructures or nanostructure branches.

Sensing Element or System:

In some embodiments, the system further comprises a sensing element (referred to herein also as a sensing system or a sensor) in fluid communication therewith, which is usable in determining a presence and/or level of the analyte, and/or or in identifying the analyte.

In some embodiments, the sensing element or system comprises a nanostructure having covalently attached thereto the capturing moiety, or any other moiety that selectively interacts with the analyte, and is configured such that upon interaction of the capturing moiety and the analyte, a detectable signal which is indicative of a presence and/or level of the analyte is generated. In some embodiments, such a sensing system is configured as field effect transistor (FET), and in some embodiments, it is a SiNW-FET.

In some embodiments, the system is a microfluidic system, and the sensing element and the separation system are in fluid communication thereamongst by means of microchannels.

The microchannels can be formed within a substrate (preferably an elastomeric substrate such as PDMS) onto which nanostructures in the sensing system are deposited.

The term "microchannel" as used herein refers to a fluid channel having cross-sectional dimensions the largest of which being less than 1 mm, more preferably less than 500 µm, more preferably less than 400 µm, more preferably less than 300 µm, more preferably less than 200 µm, e.g., 100 µm or smaller.

The microchannels can be formed in a substrate by any technique known in the art, including, without limitation, soft lithography, hot embossing, stereolithography, three-dimensional jet printing, dry etching and injection molding.

Exemplary sensing elements are as described in WO 2017/098517, which is incorporated by reference as if fully set forth herein.

Other sensing elements include, for example, analytical measurements such as a chromatographic assay, a spectroscopic assay, a spectrophotometric assay, a radioactivity assay, an electrochemical assay, an immunoassay, including, but not limited to, mass spectroscopy, high-performance liquid chromatography (HPLC), electron spin spectroscopy, a phosphorescence assay, a fluorescence assay, a chromogenic assay, a luminescence assay, a quartz crystal microbalance assay and an enzymatic assay.

The Method:

In some of any of the embodiments described herein, the system is usable, or is for use, in extracting the analyte from a liquid mixture or sample containing same.

By "extracting" it is meant separating or filtering the analyte from other components (e.g., organic and inorganic components) present in the liquid.

In some embodiments, the liquid comprises a mixture of components (e.g., organic and inorganic components). For example, a liquid mixture can comprise, addition to the analyte, a mixture of proteins, cells and/or salts.

In some embodiments, the liquid is a biological sample, for example, a whole blood sample, and the system of the present embodiments is usable for separating and/or extracting one or more analyte(s) of interest from the sample, e.g., by simply contacting the sample, as is, with the system.

The system of the present embodiments allows capturing the analyte of interest and removing all other components of the liquid mixture, and then releases the analyte, preferably into a liquid medium such as an aqueous solution, which can optionally be further analyzed by a sensing element as described herein.

In some embodiments, the extracting comprises contacting the liquid with the system, to thereby have a selective association (interaction) between the analyte and the capturing moiety, and exposing the system to light at a wavelength that generates a reactive moiety or conditions that interfere with the interaction of the capturing moiety and the analyte and/or that increase the dissociation constant between the capturing moiety and the analyte.

A system which further comprises a sensing element as described herein is usable, or is for use, in extracting the analyte from a liquid containing same and determining a presence and/or level of the analyte in the liquid.

According to an aspect of some embodiments of the present invention there is provided a method of extracting an analyte from a liquid containing same, the method comprising:

contacting the liquid (e.g., a liquid sample as described herein) with the system as described herein in any of the respective embodiments to thereby obtain a system having the analyte adsorbed to the nanostructures by means of selective interaction between the analyte and a respective capturing moiety; and exposing the system to light at a wavelength that generates reactive moiety and/or condition that interfere with the interaction between the capturing moiety and the analyte. Upon exposure to light, dissociation of the adsorbed analyte from the capturing moiety is effected, and the analyte is desorbed from the nanostructures, and is released.

In some embodiments the method comprises, during the exposing to light, contacting the system with an aqueous solution, to thereby obtain an aqueous solution containing the analyte upon its release. The aqueous solution can then be transferred to a sensing element, if present, for determining a presence and/or level of the analyte, as described herein.

In some embodiments, the exposing to light is for a time period that ranges from 1 to 1000, or from 1 to 500, or from 1 to 100, seconds, including any intermediate value and subranges therebetween.

In some embodiments, contacting the liquid with the system is for a time period that ranges from 1 to 180 minutes, or from 10 to 120 minutes.

In some embodiments, the method further comprises, subsequent to contacting the liquid with the system, washing the system with an aqueous solution.

In some embodiments, the aqueous solution is a washing buffer, which is aimed at desorption of background components from the surface of the nanostructures or nanostructure branches. Since the interactions between the analyte and the capturing moiety are stronger than the interaction of the background components with the surface of the nanostructures, the background components leave the nanostructure's surface while the marker remains.

In some embodiments, the light-activatable moiety is such that 10 minutes upon exposing to light, at least 20% of the adsorbed analyte molecules are desorbed (released).

The aqueous solutions used for washing the system and during the exposing can be the same or different, and are typically physiologically acceptable buffer solutions such as phosphate buffer solutions.

In some embodiments, the solution used during the exposure to light has a low ionic strength, e.g., lower than 0.1M.

In some embodiments, a concentration of the analyte in the liquid is less than 1 mM, or less than 1 µM, or less than 1 nM, or less than 1 pM.

According to an aspect of some embodiments of the present invention there is provided a method of determining a presence and/or a level of an analyte in a liquid, the method comprising:

subjecting the liquid to the method of extracting an analyte from the liquid, as described herein in any of the respective embodiments; and contacting the aqueous solution obtained upon the exposing with a sensing element or system configured for identifying and/or determining a presence and/or level of the analyte, as described herein.

The system of the present embodiments optionally and preferably provides a direct analysis of bio-samples on a single chip. The system of the present embodiments can selectively detect specific low abundant biomarkers, while removing unwanted components (salts, bio-molecules, proteins, cells, etc.). Preferably, the analysis is performed without performing at least one of, or more preferably without any of: centrifugation, desalting and affinity columns, since such operations are known to be time-consuming. In some embodiments of the present invention the analysis process is performed in less than 15 minutes or less than 10 minutes or less than 5 minutes.

It is to be understood that, unless otherwise defined, the operations described hereinbelow can be executed either contemporaneously or sequentially in many combinations or orders of execution. For example, two or more operations, appearing in the instant description in a particular order, can be executed in a different order (e.g., a reverse order) or substantially contemporaneously. Additionally, several operations described herein are optional and may not be executed.

The Liquid:

The liquid contacted with any one of the sensing systems as described herein can be, for example, a solution containing the analyte, or, alternatively, a solution containing a substance the produces the analyte.

Alternatively, the liquid is more complex and comprises, for example, cells, a biological sample, a biological sample comprising cells, each of which may further comprise additional agents, reagents, media and the like.

The system and method of the present embodiments can be used for separating or extracting target molecules (analytes) in many types of liquid media and objects present in liquid media. The objects can comprise organic, inorganic, biological, or any other material.

In some embodiments, the liquid is a biological sample, comprising biological components. For example, the liquid medium can comprise blood product, either whole blood or blood component. The liquid medium can alternatively, or in addition, comprise other body fluids, including, without limitation, saliva, cerebral spinal fluid, urine and the like. Also contemplated are various buffers and solutions, such as, but not limited to, nucleic acid solutions, protein solutions, peptide solutions, antibody solutions and the like.

The liquid can be a liquid that comprises blood product, either whole blood or blood component. For example, the liquid can be a blood sample.

Also contemplated are liquids containing one or more biological and chemical reagents such as, but not limited to, oxidizing agents, reducing agents, enzymes, receptor ligands, extracellular components, cellular components, metabolites, fatty acids, steroids, and the like.

A representative list of liquids from n analyte can be separated using the system and method of the present embodiments include, without limitation, water, salt water, groundwater, waste effluents, urine, blood, sperm, saliva, mucous, catemenial fluid, lymphatic fluid, cerebral spinal fluid, vaginal exudate, pus, vomit, perspiration, and inorganic liquids, including, without limitation, petroleum liquids, oils or other lubricants.

A sample as described herein can be a cellular biological sample.

Exemplary cellular biological samples include, but are not limited to, blood (e.g., peripheral blood leukocytes, peripheral blood mononuclear cells, whole blood, cord blood), a solid tissue biopsy, cerebrospinal fluid, urine, lymph fluids, and various external secretions of the respiratory, intestinal and genitourinary tracts, synovial fluid, amniotic fluid and chorionic villi.

Biopsies include, but are not limited to, surgical biopsies including incisional or excisional biopsy, fine needle aspirates and the like, complete resections or body fluids. Methods of biopsy retrieval are well known in the art.

In some embodiments, the sample is a physiological sample, drawn from a subject, for example, a blood sample or a cellular biological sample as described herein. In some of these embodiments, detecting the analyte (a bioanalyte) is effected ex vivo.

Applications:

The present inventors have designed a system and method usable for separating/extracting/filtering and optionally monitoring the presence and/or level, of a marker (an analyte) in a liquid. The system and method can be used for multiplex real-time monitoring of many types of markers in many types of liquids.

The system and method of the present embodiments can be used in many applications, including without limitation, chemical applications, genetic applications, biochemical applications, pharmaceutical applications, biomedical applications, medical applications, radiological applications and environmental applications.

For medical applications, the system and method of the present embodiments is suitable for monitoring presence, and more preferably level, of a biomarker in a biological liquid, such as a physiological solution.

For medical applications, the system and method of the present embodiments is suitable for diagnostic and patient management, as is described and exemplified hereinafter.

For environmental applications the system and method of the present embodiments is suitable for monitoring presence, and more preferably level, of markers indicative of the presence or level of hazardous materials in a liquid, such as, but not limited to, water pollutants, chemical agents, biological organisms or radiological conditions.

For genetic and biochemical applications the system and method of the present embodiments is suitable for testing and/or analysis of DNA, and other macro or smaller molecules, or reactions between such molecules in an approach known as "lab-on-chip."

A system and method as described hereinabove, can be utilized in a variety of diagnostic and therapeutic applications.

Using as the sample a biological sample as described herein of a subject in any of the embodiments of a method as described herein can be used for diagnosing a disease associated with a presence and/or level of a biomarker as described herein in the subject.

Alternatively, such a method can be used for monitoring a treatment of a disease associated with a presence and/or level of a biomarker as described herein in the subject.

In some embodiments, the method comprises contacting at least two samples with the system, and the method is being for simultaneously or sequentially determining a presence and/or an amount of the analyte in the at least two samples. In one exemplary embodiment, one sample is subjected to a therapeutic condition (e.g., medicament or treatment) and one subjected to another therapeutic condition or is not subjected to any condition, and the method allows comparing a change in the presence and/or level of a biomarker as a result of the therapeutic condition, and thus is indicative of a therapeutic efficacy of the tested therapeutic agent.

According to an aspect of some embodiments of the present invention there is provided a method of diagnosing a disease associated with a presence and/or level of a biomarker in a subject in need thereof. The method is effected by contacting a liquid physiological sample of the subject with a system as described herein.

The subject may be a healthy animal or a human subject undergoing a routine well-being check up. Alternatively, the subject may be at risk of having a disease associated with a certain biomarker (e.g., a genetically predisposed subject, a subject with medical and/or family history of a disease, a subject who has been exposed to occupational hazard or environmental hazard) and/or a subject who exhibits suspicious clinical signs of a disease.

As used herein the term "diagnosis" or "diagnosing" refers to determining presence or absence of a pathology (e.g., a disease, disorder, condition or syndrome), classifying a pathology or a symptom, determining a severity of the pathology, monitoring pathology progression, forecasting an outcome of a pathology and/or prospects of recovery and screening of a subject for a specific disease.

Determining a presence and/or amount of biomarkers can be used for determining abnormal activity in a biological sample. For example, the method can be used for detecting of overexpression of receptors associated with a disease, or for detecting a presence and/or amount of biomarkers such as antigens which are indicative of a disease.

Examples of medical conditions which can be diagnosed and/or treated according to the present teachings include, but are not limited to, cancer, pathogenic infection and autoimmune diseases. Specific examples are provided in the following.

Inflammatory diseases include, but are not limited to, chronic inflammatory diseases and acute inflammatory diseases.

Inflammatory diseases associated with hypersensitivity diseases associated with hypersensitivity such as, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH. Included are the following, as non-limiting examples:

Type I or immediate hypersensitivity, such as asthma;

Type II hypersensitivity such as, but are not limited to, rheumatoid diseases, rheumatoid autoimmune diseases, rheumatoid arthritis, spondylitis, ankylosing spondylitis, systemic diseases, systemic autoimmune diseases, systemic lupus erythematosus, sclerosis, systemic sclerosis, glandular diseases, glandular autoimmune diseases, pancreatic autoimmune diseases, diabetes, Type I diabetes, thyroid diseases, autoimmune thyroid diseases, Graves' disease, thyroiditis, spontaneous autoimmune thyroiditis, Hashimoto's thyroiditis, myxedema, idiopathic myxedema; autoimmune reproductive diseases, ovarian diseases, ovarian autoimmunity, autoimmune anti-sperm infertility, repeated fetal loss, neurodegenerative diseases, neurological diseases, neurological autoimmune diseases, multiple sclerosis, Alzheimer's disease, myasthenia gravis, motor neuropathies, Guillain-Barre syndrome, neuropathies and autoimmune neuropathies, myasthenic diseases, Lambert-Eaton myasthenic syndrome, paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies; neuropathies, dysimmune neuropathies; neuromyotonia, acquired neuromyotonia, arthrogryposis multiplex congenita, cardiovascular diseases, cardiovascular autoimmune diseases, atherosclerosis, myocardial infarction, thrombosis, granulomatosis, Wegener's granulomatosis, arteritis, Takayasu's arteritis and Kawasaki syndrome; anti-factor VIII autoimmune disease; vasculitises, necrotizing small vessel vasculitises, microscopic polyangiitis, Churg and Strauss syndrome, glomerulonephritis, pauci-immune focal necrotizing glomerulonephritis, crescentic glomerulonephritis; antiphospholipid syndrome; heart failure, agonist-like β-adrenoceptor antibodies in heart failure, thrombocytopenic purpura; hemolytic anemia, autoimmune hemolytic anemia, gastrointestinal diseases, autoimmune diseases of the gastrointestinal tract, intestinal diseases, chronic inflammatory intestinal disease, celiac disease, autoimmune diseases of the musculature, myositis, autoimmune myositis, Sjogren's syndrome; smooth muscle autoimmune disease, hepatic diseases, hepatic autoimmune diseases, autoimmune hepatitis and primary biliary cirrhosis.

Type IV or T cell mediated hypersensitivity, include, but are not limited to, rheumatoid diseases, rheumatoid arthritis, systemic diseases, systemic autoimmune diseases, systemic lupus erythematosus, glandular diseases, glandular autoimmune diseases, pancreatic diseases, pancreatic autoimmune diseases, Type 1 diabetes; thyroid diseases, autoimmune thyroid diseases, Graves' disease; ovarian diseases, prostatitis, autoimmune prostatitis, polyglandular syndrome, autoimmune polyglandular syndrome, Type I autoimmune polyglandular syndrome, neurological diseases, autoimmune neurological diseases, multiple sclerosis, neuritis, optic neuritis, myasthenia gravis, stiff-man syndrome, cardiovascular diseases, cardiac autoimmunity in Chagas' disease, autoimmune thrombocytopenic purpura, anti-helper T lymphocyte autoimmunity, hemolytic anemia, hepatic diseases, hepatic autoimmune diseases, hepatitis, chronic active hepatitis, biliary cirrhosis, primary biliary cirrhosis, nephric diseases, nephric autoimmune diseases, nephritis, interstitial nephritis, connective tissue diseases, ear diseases, autoimmune connective tissue diseases, autoimmune ear disease, disease of the inner ear, skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune diseases such as, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis, myocardial infarction, thrombosis, Wegener's granulomatosis, Takayasu's arteritis, Kawasaki syndrome, anti-factor VIII autoimmune disease, necrotizing small vessel vasculitis, microscopic polyangiitis, Churg and Strauss syndrome, pauci-immune focal necrotizing and crescentic glomerulonephritis, antiphospholipid syndrome, antibody-induced heart failure, thrombocytopenic purpura, autoimmune hemolytic anemia, cardiac autoimmunity in Chagas' disease and anti-helper T lymphocyte autoimmunity.

Examples of autoimmune rheumatoid diseases include, but are not limited to rheumatoid arthritis and ankylosing spondylitis.

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes, autoimmune thyroid diseases, Graves' disease, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

Examples of autoimmune gastrointestinal diseases include, but are not limited to, chronic inflammatory intestinal diseases, celiac disease, colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis, primary biliary cirrhosis and autoimmune hepatitis.

Examples of autoimmune neurological diseases include, but are not limited to, multiple sclerosis, Alzheimer's disease, myasthenia gravis, neuropathies, motor neuropathies; Guillain-Barre syndrome and autoimmune neuropathies, myasthenia, Lambert-Eaton myasthenic syndrome; paraneoplastic neurological diseases, cerebellar atrophy, paraneoplastic cerebellar atrophy and stiff-man syndrome; non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies; dysimmune neuropathies; acquired neuromyotonia, arthrogryposis multiplex congenita, neuritis, optic neuritis and neurodegenerative diseases.

Examples of autoimmune muscular diseases include, but are not limited to, myositis, autoimmune myositis and primary Sjogren's syndrome and smooth muscle autoimmune disease.

Examples of autoimmune nephric diseases include, but are not limited to, nephritis and autoimmune interstitial nephritis.

Examples of autoimmune diseases related to reproduction include, but are not limited to, repeated fetal loss.

Examples of autoimmune connective tissue diseases include, but are not limited to, ear diseases, autoimmune ear diseases and autoimmune diseases of the inner ear.

Examples of autoimmune systemic diseases include, but are not limited to, systemic lupus erythematosus and systemic sclerosis.

Infectious diseases such as, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft rejection diseases including diseases associated with transplantation of a graft such as, but are not limited to, graft rejection, chronic graft rejection, subacute graft rejection, hyperacute graft rejection, acute graft rejection and graft versus host disease.

Allergic diseases which include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous diseases include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, paccreas, cervix, prostate, and ovarian.

According to an aspect of some embodiments of the invention there is provided a method of disease treatment in a subject in need thereof, the method comprising:

(a) diagnosing a presence of the disease in the subject according to the method described herein; and (b) treating the subject based on the diagnosis.

Embodiments of the present invention have a variety of applications pertaining to individually optimizing disease treatment, monitoring disease treatment in a subject, determining a treatment for a subject and identifying an agent capable of treating a disease in a subject.

As used herein throughout, for any of the relevant embodiments described herein, a "therapy" or "treatment" describes a therapeutic agent, which is also referred to herein as a medicament, as well as other treatments such as, for example, radiation, dehydration, devitalization, and the like.

According to an aspect of some embodiments of the present invention there is provided a method of monitoring disease treatment in a subject, the method comprising:

(a) administering at least one medicament against the disease to the subject; and
(b) determining a level of one or more bioanalytes in the sample, wherein a shift in the level of the one or more bioanalytes in the sample towards that of a normal healthy sample examined under identical conditions is indicative of an efficacious treatment of the disease.

According to a specific embodiment, "a shift in the level of an analyte in the cell towards that of a normal healthy cell sample examined under identical conditions" refers to at least a 10% local or global (throughout the profile) shift preferably towards 100% identity to the control normal healthy cell sample.

A shift beyond a predetermined threshold as will be determined by the skilled artisan as indicative of an efficacious treatment.

It is expected that during the life of a patent maturing from this application many relevant photo-activatable moieties, capturing moieties, substrates and nanostructures will be developed and the scope of the terms photo-activatable moiety, capturing moiety, substrate and nanostructure is intended to include all such new technologies a priori.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein throughout, the phrase "linking moiety" or "linking group" describes a group that connects two or more moieties or groups in a compound. A linking moiety is typically derived from a bi- or tri-functional compound, and can be regarded as a bi- or tri-radical moiety, which is connected to two or three other moieties, via two or three atoms thereof, respectively.

Exemplary linking moieties include a hydrocarbon moiety or chain, optionally interrupted by one or more heteroatoms, as defined herein, and/or any of the chemical groups listed below, when defined as linking groups.

When a chemical group is referred to herein as "end group" it is to be interpreted as a substituent, which is connected to another group via one atom thereof.

Herein throughout, the term "hydrocarbon" collectively describes a chemical group composed mainly of carbon and hydrogen atoms. A hydrocarbon can be comprised of alkyl, alkene, alkyne, aryl, and/or cycloalkyl, each can be substituted or unsubstituted, and can be interrupted by one or more heteroatoms. A hydrocarbon can be a linking group or an end group.

As used herein, the term "amine" describes both a —NRxRy group and a —NRx- group, wherein Rx and Ry are each independently hydrogen, alkyl, cycloalkyl, aryl, as these terms are defined hereinbelow.

The amine group can therefore be a primary amine, where both Rx and Ry are hydrogen, a secondary amine, where Rx is hydrogen and Ry is alkyl, cycloalkyl or aryl, or a tertiary amine, where each of Rx and Ry is independently alkyl, cycloalkyl or aryl.

Alternatively, Rx and Ry can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NRxRy group in cases where the amine is an end group, as defined hereinunder, and is used herein to describe a —NRx- group in cases where the amine is a linking group or is or part of a linking moiety.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms (C(1-4) alkyl). The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain. When the alkyl is a linking group, it is also referred to herein as "alkylene" or "alkylene chain".

Alkene and alkyne, as used herein, are an alkyl, as defined herein, which contains one or more double bond or triple bond, respectively.

The term "cycloalkyl" describes an all-carbon monocyclic ring or fused rings (i.e., rings which share an adjacent pair of carbon atoms) group where one or more of the rings does not have a completely conjugated pi-electron system. Examples include, without limitation, cyclohexane, adamantine, norbornyl, isobornyl, and the like. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofurane, tetrahydropyrane, morpholino, oxalidine, and the like. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "halide" and "halo" describes fluorine, chlorine, bromine or iodine.

The term "haloalkyl" describes an alkyl group as defined above, further substituted by one or more halide.

The term "sulfate" describes a —O—S(=O)$_2$—ORx end group, as this term is defined hereinabove, or an —O—S(=O)$_2$—O— linking group, as these phrases are defined hereinabove, where Rx is as defined hereinabove.

The term "thiosulfate" describes a —O—S(=S)(=O)—ORx end group or a —O—S(=S)(=O)—O— linking group, as these phrases are defined hereinabove, where Rx is as defined hereinabove.

The term "sulfite" describes an —O—S(=O)—O-Rx end group or a —O—S(=O)—O— group linking group, as these phrases are defined hereinabove, where Rx' is as defined hereinabove.

The term "thiosulfite" describes a —O—S(=S)—O—Rx end group or an —O—S(=S)—O— group linking group, as these phrases are defined hereinabove, where Rx is as defined hereinabove.

The term "sulfinate" describes a —S(=O)—ORx end group or an —S(=O)—O— group linking group, as these phrases are defined hereinabove, where Rx is as defined hereinabove.

The term "sulfoxide" or "sulfinyl" describes a —S(=O)Rx end group or an —S(=O)— linking group, as these phrases are defined hereinabove, where Rx is as defined hereinabove.

The term "sulfonate" describes a —S(=O)$_2$-Rx end group or an —S(=O)$_2$— linking group, as these phrases are defined hereinabove, where Rx is as defined herein.

The term "S-sulfonamide" describes a —S(=O)$_2$—NRxRy end group or a —S(=O)$_2$—NRx- linking group, as these phrases are defined hereinabove, with Rx and Ry as defined herein.

The term "N-sulfonamide" describes an RxS(=O)$_2$—NRy- end group or a —S(=O)$_2$—NRx- linking group, as these phrases are defined hereinabove, where Rx and Ry are as defined herein.

The term "disulfide" refers to a —S—SRx end group or a —S—S— linking group, as these phrases are defined hereinabove, where Rx is as defined herein.

The term "phosphonate" describes a —P(=O)(ORx)(ORy) end group or a —P(=O)(ORx)(O)— linking group, as these phrases are defined hereinabove, with Rx and Ry as defined herein.

The term "thiophosphonate" describes a —P(=S)(ORx)(ORy) end group or a —P(=S)(ORx)(O)— linking group, as these phrases are defined hereinabove, with Rx and Ry as defined herein.

The term "phosphinyl" describes a —PRxRy end group or a —PRx- linking group, as these phrases are defined hereinabove, with Rx and Ry as defined hereinabove.

The term "phosphine oxide" describes a —P(=O)(Rx)(Ry) end group or a —P(=O)(Rx)- linking group, as these phrases are defined hereinabove, with Rx and Ry as defined herein.

The term "phosphine sulfide" describes a —P(=S)(Rx)(Ry) end group or a —P(=S)(Rx)- linking group, as these phrases are defined hereinabove, with Rx and Ry as defined herein.

The term "phosphite" describes an —O—PRx(=O)(ORy) end group or an —O—PRx(=O)(O)— linking group, as these phrases are defined hereinabove, with Rx and Ry as defined herein.

The term "carbonyl" or "carbonate" as used herein, describes a —C(=O)—Rx end group or a —C(=O)— linking group, as these phrases are defined hereinabove, with Rx as defined herein.

The term "thiocarbonyl" as used herein, describes a —C(=S)—Rx end group or a —C(=S)— linking group, as these phrases are defined hereinabove, with Rx as defined herein.

The term "oxo" as used herein, describes a (=O) group, wherein an oxygen atom is linked by a double bond to the atom (e.g., carbon atom) at the indicated position.

The term "thiooxo" as used herein, describes a (=S) group, wherein a sulfur atom is linked by a double bond to the atom (e.g., carbon atom) at the indicated position.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The "hydroxyalkyl" is also referred to herein as "alcohol", and describes an alkyl, as defined herein, substituted by a hydroxy group.

The term "cyano" describes a —C≡N group.

The term "isocyanate" describes an —N=C=O group.

The term "isothiocyanate" describes an —N=C=S group.

The term "nitro" describes an —NO$_2$ group.

The term "acyl halide" describes a —(C=O) Rz group wherein Rz is halide, as defined hereinabove.

The term "azo" or "diazo" describes an —N=NRx end group or an —N=N— linking group, as these phrases are defined hereinabove, with Rx as defined hereinabove.

The term "peroxo" describes an —O—ORx end group or an —O—O— linking group, as these phrases are defined hereinabove, with Rx as defined hereinabove.

The term "carboxylate" as used herein encompasses C-carboxylate and O-carboxylate.

The term "C-carboxylate" describes a —C(=O)—ORx end group or a —C(=O)—O— linking group, as these phrases are defined hereinabove, where Rx is as defined herein.

The term "O-carboxylate" describes a —OC(=O)Rx end group or a —OC(=O)— linking group, as these phrases are defined hereinabove, where Rx is as defined herein.

A carboxylate can be linear or cyclic. When cyclic, Rx and the carbon atom are linked together to form a ring, in C-carboxylate, and this group is also referred to as lactone. Alternatively, Rx and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and O-thiocarboxylate.

The term "C-thiocarboxylate" describes a —C(=S)—ORx end group or a —C(=S)—O— linking group, as these phrases are defined hereinabove, where Rx is as defined herein.

The term "O-thiocarboxylate" describes a —OC(=S)Rx end group or a —OC(=S)— linking group, as these phrases are defined hereinabove, where Rx is as defined herein.

A thiocarboxylate can be linear or cyclic. When cyclic, Rx and the carbon atom are linked together to form a ring, in C-thiocarboxylate, and this group is also referred to as thiolactone. Alternatively, Rx and O are linked together to form a ring in O-thiocarboxylate. Cyclic thiocarboxylates can function as a linking group, for example, when an atom in the formed ring is linked to another group.

The term "carbamate" as used herein encompasses N-carbamate and O-carbamate.

The term "N-carbamate" describes an RyOC(=O)—NRx- end group or a —OC(=O)—NRx- linking group, as these phrases are defined hereinabove, with Rx and Ry as defined herein.

The term "O-carbamate" describes an —OC(=O)—NRxRy end group or an —OC(=O)—NRx- linking group, as these phrases are defined hereinabove, with Rx and Ry as defined herein.

A carbamate can be linear or cyclic. When cyclic, Rx and the carbon atom are linked together to form a ring, in O-carbamate. Alternatively, Rx and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and O-thiocarbamate.

The term "O-thiocarbamate" describes a —OC(=S)—NRxRy end group or a —OC(=S)—NRx- linking group, as these phrases are defined hereinabove, with Rx and Ry as defined herein.

The term "N-thiocarbamate" describes an RyOC(=S)NRx- end group or a —OC(=S)NRx- linking group, as these phrases are defined hereinabove, with Rx and Ry as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(=S)—NRxRy end group or a —SC(=S)NRx- linking group, as these phrases are defined hereinabove, with Rx and Ry as defined herein.

The term "N-dithiocarbamate" describes an RySC(=S)NRx- end group or a —SC(=S)NRx- linking group, as these phrases are defined hereinabove, with Rx and Ry as defined herein.

The term "urea", which is also referred to herein as "ureido", describes a —NRxC(=O)—NRyRq end group or a —NRxC(=O)—NRy- linking group, as these phrases are defined hereinabove, where Rz and Ry are as defined herein and Rq is as defined herein for Rx and Ry.

The term "thiourea", which is also referred to herein as "thioureido", describes a —NRx-C(=S)—NRyRq end group or a —NRx-C(=S)—NRy- linking group, with Rx, Ry and Rq as defined herein.

The term "amide" as used herein encompasses C-amide and N-amide.

The term "C-amide" describes a —C(=O)—NRxRy end group or a —C(=O)—NRx- linking group, as these phrases are defined hereinabove, where Rx and Ry are as defined herein.

The term "N-amide" describes a RxC(=O)—NRy- end group or a RxC(=O)—N— linking group, as these phrases are defined hereinabove, where Rx and Ry are as defined herein.

An amide can be linear or cyclic. When cyclic, Rx and the carbon atom are linked together to form a ring, in C-amide, and this group is also referred to as lactam. Cyclic amides can function as a linking group, for example, when an atom in the formed ring is linked to another group.

The term "guanyl" describes a RxRyNC(=N)— end group or a —RxNC(=N)— linking group, as these phrases are defined hereinabove, where Rx and Ry are as defined herein.

The term "guanidine" describes a —RxNC(=N)—NRyRq end group or a —RxNC(=N)—NRy- linking group, as these phrases are defined hereinabove, where Rx, Ry and Rq are as defined herein.

The term "hydrazine" describes a —NRx-NRyRq end group or a —NRx-NRy- linking group, as these phrases are defined hereinabove, with Rx, Ry, and Rq as defined herein.

As used herein, the term "hydrazide" describes a —C(=O)—NRx-NRyRq end group or a —C(=O)—NRx-NRy- linking group, as these phrases are defined hereinabove, where Rx, Ry and Rq are as defined herein.

As used herein, the term "thiohydrazide" describes a —C(=S)—NRx-NRyRq end group or a —C(=S)—NRx-NRy- linking group, as these phrases are defined hereinabove, where Rx, Ry and Rq are as defined herein.

As used herein, the term "alkylene glycol" describes a —O—[(CRxRy)$_z$-O]$_y$-Rq end group or a —O—[(CRxRy)$_z$-O]$_y$— linking group, with Rx, Ry and Rq being as defined herein, and with z being an integer of from 1 to 10, preferably, 2-6, more preferably 2 or 3, and y being an integer of 1 or more. Preferably Rx and Ry are both hydrogen. When z is 2 and y is 1, this group is ethylene glycol. When z is 3 and y is 1, this group is propylene glycol.

When y is greater than 4, the alkylene glycol is referred to herein as poly(alkylene glycol). In some embodiments of the present invention, a poly(alkylene glycol) group or moiety can have from 10 to 200 repeating alkylene glycol units, such that z is 10 to 200, preferably 10-100, more preferably 10-50.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Fabrication of Silicon Nanowire Forest (SiNW Forest)

Silicon nanowire forest was fabricated as described in Krivitsky et al., *Nano Lett* 2012 (supra).

In brief, a large scale densely packed monolayer of polystyrene beads of 0.5 μm diameter is formed through a simple spin coating process on the silicon substrate. The beads monolayer is further subjected to a dry plasma etching step, therefore reducing the diameter of individual beads and increasing their array interdistance (200-300 nm diameter and about 200 nm inter-bead distance). Careful modulation of the plasma parameters applied allows controlling the diameter of the resulting nanobeads, as well as their morphology, leading to beads with teeth-like rough edges, showing different roughness extents. A metal-assisted wet etching process is applied for the creation of the vertical nanowire forests, using evaporated silver metal film as catalyst, and $HF/H_2O_2$ as etchant and oxidant, respectively.

This etching step allows the control over the length of nanowire elements, 3-20 μm, as well as the morphology of the resulting wires, by the formation of rough/nanoporous SiNW elements, depending on the experimental conditions applied. The morphology of obtained etched beads, used as masks for the subsequent wet etching formation of the SiNWs forests, dictates the final shape of the resulting nanowires; the shape of the masking bead being reflected on the newly formed wires. The use of star-shaped rough beads is preferential when higher active surface for the binding of biomolecules is required, thus increasing the roughness extent of the resulting substrate. Aggressive etching of PS bead elements leads to holey PS masks, which in turn lead to the formation of nanowire elements of extreme roughness and porosity with tube-like hollow structures.

After the nanowire forests are formed, the metal catalyst layer and beads are removed before further modification of NWs surfaces.

Both the shape of the polystyrene bead nanomasks and the subsequent metal-assisted etching step contribute to the final increased roughness and porosity of the resulting Si posts.

Using this methodology, a planar device of 1 $cm^2$ geometric surface area can convert into a filtering device of about 150-300 $cm^2$ after the formation of the NWs forest (with nanowires of 5-10 μm height, 250 nm diameter, 250 nm inter-NW distance and roughness factor of 8), a 150-300-fold larger active surface than the planar counterpart. Higher NW forests, up to 50 µm, with increased roughness/porosity can clearly lead to higher effective biomolecular binding areas. Forests of smooth nanowire elements only bring to a 17-30-fold surface increase, an order of magnitude lower than the roughed SiNW counterparts.

The resulting NWs, featuring increased active surfaces, improve the extent of biomolecules binding in subsequent steps, allowing for larger biomolecule amounts to bind to the NW-based capturing forests.

The bare as-resulting SiNW forests reveal low wetting capabilities, exhibiting hydrophobic-like characteristics. Chemical modification of the substrate with the aminosilane derivative (3-aminopropyl)-dimethyl-ethoxysilane (APDMES), leads to surfaces exhibiting optimal wetting capabilities for biological applications.

A successful modification of Si nanowire elements is achieved along their whole length, as evident from representative SEM images obtained from the incubation of positively charged amino-modified NWs with negatively charged gold nanoparticles solution (not shown). Gold nanoparticles elements clearly adhere homogeneously along NWs surfaces, in contrast to the negligible adhesion of nanoparticles on the unmodified surfaces of low-wettability.

SiNW forests decorated with controllable densities of Au nanoparticles can be used for modification of the SiNWs by biomolecules, through a thiol-Au chemistry, and also in further increasing the surface area of nanowire forests, as is further detailed hereinafter.

The steps utilized in the fabrication of SiNW forest are as follows:

Wafers Cleaning:
Immerse the wafer in acetone 20 ml, sonicate for 2 minutes and dry with $N_2$;
Immerse the wafer in isopropanol 20 ml, sonicate for 2 minutes and dry with $N_2$; and
Immerse the wafer in fresh piranha solution for 4 minutes, wash the wafer with DI water and dry with $N_2$.

Preparation of 1% Polystyrene Beads Suspension:
Take 0.385 ml of 2.6% Polystyrene beads suspension (0.5 µm, Polyscience) and centrifuge it at 4500 rpm for 16 minutes;
Separate the Polystyrene beads carefully with pipette Pasteur from water and add 1 ml of methanol and 0.3 mg TWEEN 80 on Polystyrene beads (3% mass percent of TWEEN 80 on Polystyrene beads mass). The (preferably fresh) solution has: 0.3 mg TWEEN 80, 10 mg Polystyrene beads and 1 ml methanol; and
Disperse suspension (preferably using "Vortex", without ultrasonic disperser which may lead to Polystyrene beads destruction and agglomeration).

Deposition of the Polystyrene Beads:
Take the needed amount (18-20 µl for wafer 2×2 $cm^2$, 200 µl for wafer 4×4 $cm^2$) of a well-shaked suspension with pipettor, drip it slowly from a low height in the center of the wafer, wait for a full spreading of the suspension (1-2 seconds) and start spin coating, adjust the spin rate and time according to wafer dimension (for 2×2 $cm^2$ 1 minute at 475 rpm; For 4×4 $cm^2$ 2 minutes at 180 rpm).

Polystyrene Beads Plasma Etching (PECVD):
Conditions: $O_2$=50 sccm, P=40 mtorr, Bias=15-50 w, time=3-15 minutes (for about 200-300 nm SiNWs). For good quality take for one batch 4 wafers only in the center of the chamber.

E-Beam Ag-Film Deposition:
Thickness 45 nm, deposition rate 1 A/sec.

Silicon Wafer Wet Etching:
Etching solution: HF=4.6M, $H_2O_2$=0.44M in $H_2O$. After 9 minutes etching SiNWs with a length of 3 microns are obtained;
Rinse the wafer with DI water.

Ag-Wet Etching:
Drip 2-3 drops of $HNO_3$ (69%) to wafer, wait for 10 minutes and rinse it with DI water. Rinse the wafer with IPA and dry at 100° C.

Polystyrene Beads Finishing Plasma Etching:
Plasma conditions: P (02)=0.2 Torr, t=10 minutes, bias=100 w, put the wafer directly on aluminum chamber (300 nm Polystyrene beads diameter).

Example 2

Fabrication of 3D Branched Silicon Nanowire Matrix (BSiNW Forest)

A silicon nanowire forest was fabricated as described in Example 1, and in Krivitsky et al. *Nano Lett* 2012 (supra), and was subjected to oxygen plasma (100 Watt) for 10 minutes. Then, gold nanoparticles were deposited on the silicon surface by electroless deposition, using 20% DIW, 80% ethanol, 0.05 M HF, 110 µM $NaAuCl_4$, 1% TWEEN 80 (200 µl) for 30 minutes. Finally, 3D SiNW branches were grown in a chemical vapor deposition (CVD) device by vapor liquid process (VLS) using $SiH_4$ as silicon precursor, under the following conditions: Vacuum for 15 minutes; 25 SCCM argon, 25 Torr at 460° C. for 15 minutes; 20 SCCM argon 5 SCCM $SiH_4$, 25 Torr at 460° C. for 2 minutes; 25 SCCM argon for 15 minutes.

FIG. 2 presents SEM images of SiNWF (left), SiNWF in which gold nanoparticles are deposited on the nanowires' surface (middle), and of the obtained 3D branched SiNW matrix.

FIGS. 3A-B present SE (FIG. 3A) and BSE (FIG. 3B) images of SiNWF in which gold nanoparticles are deposited on the nanowires' surface.

FIGS. 4A-D present SE images of Branched Si Nanowires Forest (BSiNWF) at different magnifications Example 3

Modification of SiNW Forest with a Light-Sensitive Moiety and a Biorecognition Capturing Moiety 8-Acetoxy-pyrene-1,3,6-trisulfonyl chloride was synthesized for providing HPTS (8-hydroxypyrene-1,3,6-trisulfonic acid) as a light sensitive moiety covalently attached to the SiNW.

Synthesis of 8-acetoxy-pyrene-1,3,6-trisulfonyl Chloride

Trisodium-1-hydroxypyrene-1,3,6-trisulfonate (20 grams, 0.038 mol) was dissolved in a solution of NaOH (2.4 grams, 0.06 mol) in water (30 ml), and then cooled to about 0° C. Acetic anhydride (5 grams, 4.8 ml, 0.48 mol) was added dropwise to the solution, and the reaction mixture was stirred for 2 hours. Ethanol (20 ml) was added to complete a precipitation, the precipitate was collected by filtration, washed with ethanol (3×10 ml), and dried under reduced pressure for 24 hours to obtain a yellow solid (17 grams, 78.7% yield). A mixture of trisodium-8-acetoxy-pyrene-1,3,6-trisulfonate (5 grams, 0.0088 mol) and toluene (150 ml)

was placed in 0.25 liter round-bottomed flask, equipped with an automatic water separator (Dean-Stark trap) and a condenser. The mixture was heated under reflux for 2 hours to dry the reaction mixture. Then it was cooled to 60° C. and oxalyl chloride (6 ml) and DMF (2 drops) were added. The mixture was heated under reflux for 8 hours, and a mixture of toluene and oxalyl chloride excess (30 ml) was distilled. A precipitate of sodium-chloride was collected by filtration and the solvent was removed from the filtrate under reduce pressure. A solid residue was dried in vacuum for 24 hours to give trichloride (4 grams; 81.5% yield). MS (m/e): [M]+555.8 ($C_{16}H_7Cl_3O_7S_3$).

Antibody and HPTS Immobilization on Silicon Nanowire Forest Wafer:

Clean with acetone, DI water and IPA. Dry gently with $N_2$;

Plasma treatment for 30 minutes, 100 W, 0.200 Torr $O_2$;
APDMES modification: 100% APDMES, 50° C., 3 hours;
Wash with IPA;
Dehydration: 115° C., 30 minutes;

The nanowire forest substrate was modified with an 8-acetoxy-pyrene-1,3,6-trisulfonyl chloride layer. 24 hours incubation with 8-acetoxy-pyrene-1,3,6-trisulfonyl chloride and pyridine, and then exposure of the phenol function group with saturated sodium bicarbonate solution;

Dialysis: 10-100 µg/ml of antibody in phosphate buffer (PB) (10 mM, pH=8.5), 5 hours, change solution every 20 minutes, dialysis volume 50 ml;

Glutaraldehyde modification: 8.3% glutaraldehyde containing 12 mM sodium cyanoborohydride, for 3 hours;

Wash with: DI, acetone, IPA and DI again;

Ab modification: Antibody (from dialysis) in PB (10-100 µg/ml), containing 12 mM sodium cyanoborohydride, at 4° C., for overnight on nanowire forest wafer;

Blocking: ethanolamine (100 mM) containing 12 mM sodium cyanoborohydride in PB (pH 8.6), for 3 hours under shaking about 30 RPM; and Wash with PB.

Example 4

Fabrication of SiNW FETs Sensing System

Fabrication of SiNW FET:

Silicon nanowires were synthesized by chemical vapor deposition as previously described. In short, 20 nm gold nanoparticles (Ted Pella), which served as catalyst sites for the VLS-CVD growth of Si nanowires, were initially deposited on Si (100) growth substrates. To promote the adhesion of the gold nanoparticles to the silicon substrate, a poly-L-lysine solution (Ted Pella) was applied to the bare silicon wafer, as an electrostatic binding agent. The nanoparticle-decorated wafer was then placed in a horizontal tube furnace for the growth of the SiNWs. Silane and diborane were used as reactants during the growth to provide boron as a p-type dopant with a B:Si ratio of 1:4000.

FETs based on antibody-modified SiNW elements were fabricated by standard photolithography procedures. Firstly, the sensor device was cleaned with acetone and isopropyl alcohol, followed by oxygen plasma treatment. Briefly, modified NWs were transferred to the sensor chip, and source and drain electrodes were deposited by the use of a multilayer resist structure consisting of 300 nm LOR-5A copolymer and 500 nm S-1805 photoresist (purchased from MicroChem Corp.). After exposure and development of the electrode pattern, the contacts were metallized by e-beam evaporation of Ti/Pd/Ti (5/60/10 nm) respectively, and were then passivated from the electrolyte with an insulating layer of $Si_3N_4$ (65 nm-thick) deposited by Inductively Coupled Plasma Enhanced Chemical Vapor Deposition (ICP-PECVD), and a thin alumina layer, 5 nm, deposited by ALD (Cambridge Nanotech).

Nanowire-FET Device Surface Modification with Antibodies:

Wash the chip with acetone, DI water and IPA;
Plasma 30 minutes, 100 W, 0.200 Torr $O_2$;
APDMES modification: 100% APDMES, 50° C., 30 minutes;
Wash with IPA;
Dehydration: 115° C., 25 minutes;
Dialysis: 40 µg of antibody in 200 µl (200 µg/ml) PB (10 mM, pH=8.5);
glutaraldehyde modification: 8.3% glutaraldehyde containing 12 mM sodium cyanoborohydride, reaction time 30 minutes, under shaking 30 rpm, cover from light during the reaction;
Chip wire-bonding;
Assemble a PDMS channel (see below);
Ab modification: an antibody (e.g., Anti-cTnT) in PB (16 µg/ml), containing 12 mM sodium cyanoborohydride, at 4° C., flow at 2~2.4 µl/minute for overnight;
Blocking: ethanolamine (100 mM) containing 12 mM sodium cyanoborohydride (pH8.67), flow at 5 µl/min for 3 hours;
Flow sensing buffer (SB) (e.g., 10 µM phosphate buffer pH=8.00) at 5 µl/minute for 30 minutes to wash the channel, then do transconductance test. Generally, a sensing buffer is a low ionic strength solution—of less than 1 mM.

Fluid-Delivery System:

The fluid-delivery system was fabricated from flexible polydimethylsiloxane (PDMS) elastomer mixed in a 10:1 ratio with base as curing agent. The PDMS was cured overnight in an oven at 60° C. and then cut into rectangular pieces. The dimensions of the PDMS were 10×10×5 mm.

Data Acquisition, Electrical Setup and Sensing:

The basic electrical properties of the SiNW devices on the sensor chip were first characterized in air as this provides means for quality control before completion of the sensor structure. Then, the sensor device chip was integrated with a custom-made PDMS microfluidic channel and wire bonded to the outside conductive pads for the electrical measurements. The conductance of the SiNW-FET was measured by a DC custom-made electronic board of 64 measuring channels. The drain current was amplified and filtered. The action of injecting the solution might introduce some noise into the electrical read-out signal. All studies were carried out at room temperature.

Example 5

Capturing and Sensing

Materials and Methods:

CA 15.3 capturing and sensing:

Incubation: incubate 5.35 pM CA 15-3 in sensing buffer (PB 100 µM) on SiNWs forest capturing wafer, immobilized with anti-CA 15.3, anti-hemoglobin and anti-eGFP, as follows:

(1) 30 µg/cm$^2$ anti-Human hemoglobin, (2) 30 µg/cm$^2$ anti-eGFP and (3) 30 µg/cm$^2$ anti-CA 15-3);

Washing: 5 seconds with sensing buffer via squeeze bottle (about 30 ml) (flow of 500 µl/minute);

Elution in 100 μm PB: incubate SiNW forest in sensing buffer and irradiate light (LED light emitter power 43 mW at 385 nm);

Sensing: flow the eluted solution from the wafer into sensing system. Vg=0 V, Vds=0.2 V, flow rate=10 μl/minute.

Human Hemoglobin Capturing and Sensing:

Incubation: incubate human hemoglobin in phosphate-buffered saline on SiNWs forest capturing wafer, immobilized with anti-hemoglobin;

Washing: 5 seconds with sensing buffer via squeeze bottle (about 30 ml);

Elution: incubate NW forest in sensing buffer and irradiate light (LED light emitter power 43 mW at 385 nm);

The absorbance was measured at 406 nm using a commercial fluorescence scanner (TECAN Infinite M200).

eGFP Capturing and Sensing:

Incubation: incubate e-GFP in phosphate-buffered saline on SiNWs forest capturing wafer, immobilized with 30 μg/cm$^2$ anti-eGFP;

Washing: 5 seconds with sensing buffer via squeeze bottle (about 30 ml);

Elution: incubate NW forest in sensing buffer and irradiate light (LED light emitter power 43 mW at 385 nm); The fluorescence was measured at 517 nm using a commercial fluorescence scanner (TECAN Infinite M200).

eGFP Capturing and Sensing in Blood Sample:

A human blood sample was spiked by eGFP (30 μl eGFP were added to 1710 μl blood so as to obtain 0.6 μM eGFP spiked-blood. Capturing and sensing was performed on SiNWs forest capturing wafer, immobilized with anti-CA 15.3, anti-hemoglobin and anti-eGFP 30 μg/cm$^2$ each, as described hereinabove.

Adsorption and Desorption Studies:

Adsorption-desorption kinetic measurements were performed as described in Krivitsky et al., *Nano Lett* 2012 (supra).

Adsorption and desorption studies were performed in sensing buffer (100 μM Phosphate buffer (PB)) via SiNW sensing as described in Krivitsky et al., *Nano Lett* 2012 (supra).

Results:

Adsorption and Desorption of CA 15-3 (Carcinoma Antigen 15-3):

FIGS. 5A-B present the data obtained for adsorption of CA 15-3 on anti-CA 15-3-, anti-hemoglobin-, anti-eGFP- and HTPS-modified SiNW forest from a solution containing 5.35 pM of the antigen in the sensing buffer as a function of incubation time, by percents (%) of the adsorbed antigen out of the total amount of the antigen in the solution (FIG. 5A) and by the concentration of the adsorbed antigen out of the total amount of the antigen in the solution (FIG. 5B), showing 100% adsorption upon 10 minutes incubation.

FIG. 6 presents the original signals generated by the modified SiNW forest device during the adsorption of the CA 15-3 solution, showing the sensing (current vs time) of CA-153 protein adsorption to SiNW forest-based capturing device, as a function of time, as detected by respective coupled SiNW FET sensing arrays. Baseline represents the current detected in the presence of a 'sensing buffer' solution.

As seen, all 5.35 pM of CA-15.3 were adsorbed after 10 minutes, as shown by detected current values which are the same as for pure sensing buffer (baseline) and 10 minutes after the CA-15.3-spiked introduced to SiNW forest-based capturing element.

FIGS. 7A-B present the desorption of CA 15-3 from the modified SiNW forest device upon application of light irradiation (HPTS excitation), by percents (%) of the desorbed antigen (FIG. 7A) and by the concentration of the desorbed antigen (FIG. 7B), showing that more than 80% of the adsorbed antigen are released 10 minutes upon radiation.

FIG. 8 presents the original signals generated by the modified SiNW forest device during the desorption of the adsorbed CA 15-3 solution, showing the sensing (current vs time) of CA-153 protein released from the SiNW forest-based capturing device, as a function of radiation time, as detected by the coupled SiNW FET sensing arrays. Baseline represents 'sensing buffer' solution.

Adsorption and Desorption of eGFP:

FIG. 9 presents a calibration curve of the fluorescence emission intensity of eGFP as a function of its concentration, showing a linear correlation. Inset shows log-log plot of the calibration curve.

FIG. 10 presents a graph showing adsorption kinetics of eGFP on SiNW forest surface modified with anti-eGFP and HTPS.

FIG. 11 presents a graph showing the desorption kinetics of the adsorbed eGFP when exposed to light (dark gray squares) and at dark (light gray circles), showing about 100% desorption 10 minutes upon irradiation, compared to less than 20% desorption at dark.

Adsorption and Desorption of Hemoglobin:

FIG. 12 presents comparative plots showing the adsorption kinetics of hemoglobin to SiNW forest surface modified with anti-hemoglobin (light gray circles) and with anti-hemoglobin and HPTS (dark gray squares). As shown therein, the HPTS modification on SiNW forest does not influence drastically the capturing capabilities of the SiNW forest.

FIG. 13 presents the desorption kinetics of the adsorbed hemoglobin when exposed to light (dark gray squares) and at dark (light gray circles), showing about 100% desorption less than 5 minutes upon irradiation, compared to less than 5% desorption at dark.

Adsorption and Desorption of Hemoglobin Using Branched SiNW Forest:

FIG. 14 presents comparative plots showing the improved adsorption of hemoglobin to branched SiNW forest surface modified with anti-hemoglobin and HPTS, compared to similarly modified SiNW forest.

FIG. 15 presents the desorption of the hemoglobin adsorbed to branched SiNW forest when exposed to light, showing release of more than 20% of the adsorbed hemoglobin 11 minutes upon irradiation.

Adsorption and Desorption of eGFP from Blood Sample:

FIG. 16 presents a graph showing the desorption kinetics of eGFP from a blood sample spiked with eGFP absorbed to SiNW forest surface modified with anti-eGFP and HPTS, when exposed to light (light gray circles) and at dark (dark gray rectangulars), showing about 100% desorption 10 minutes upon irradiation, compared to no desorption at dark.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system comprising a substrate and a multiplicity of nanostructures arranged on the substrate at a density of at least 100,000 nanostructures per 1 cm$^2$, each nanostructure in at least a first portion of said nanostructures featuring a capturing moiety covalently attached to a surface thereof and each nanostructure in at least a second portion of said nanostructures featuring a light-activatable moiety covalently attached to a surface thereof, wherein said capturing moiety selectively interacts with an analyte, and said light-activatable moiety generates, upon exposure to light, a reactive moiety that interferes with an interaction of said capturing moiety and said analyte, said reactive moiety being such that induces a release of at least 20% of molecules of said analyte that interact with said capturing moieties in 10 minutes.

2. The system of claim 1, wherein at least one of said nanostructures has both said capturing moiety and said light-activatable moiety covalently attached to a surface thereof.

3. The system of claim 1, wherein said analyte is a biomarker.

4. The system of claim 3, wherein said capturing moiety is a first member of an affinity pair and said analyte is a second member of said affinity pair.

5. The system of claim 4, wherein said affinity pair is selected from an antigen-antibody pair, a receptor-ligand pair, an enzyme-substrate pair, a streptavidin-biotin pair, a protein-cofactor pair, a protein-protein pair, and pairs of complementary oligonucleotides, or of complementary oligonucleotide-peptide nucleic acid.

6. The system of claim 1, wherein said capturing moiety is an antibody and said analyte selectively interacts with said antibody.

7. The system of claim 6, wherein said analyte is an antigen.

8. The system of claim 1, wherein said capturing moiety and said analyte feature a pH-dependent dissociation constant.

9. The system of claim 8, wherein said light-activatable moiety generates, upon said exposure to light, a reactive moiety that induces a change in protons concentration in proximity to said at least a portion of said nanostructures that features said capturing moiety.

10. The system of claim 8, wherein said light-activatable moiety generates, upon said exposure to light, protons.

11. The system of claim 1, wherein said light-activatable moiety generates, upon said exposure to light, a reactive moiety that induces a change in protons concentration in proximity to said at least a portion of said nanostructures that features said capturing moiety.

12. The system of claim 1, wherein said light-activatable moiety generates, upon said exposure to light, protons.

13. The system of claim 1, wherein said nanostructures are generally parallel to each other.

14. The system of claim 1, wherein said nanostructures are aligned generally vertically to said substrate.

15. The system of claim 1, wherein an average inter-distance between said nanostructures ranges from 10 nm to 10000 nm.

16. The system of claim 1, wherein at least a portion of said nanostructures comprises branched nanostructures.

17. The system of claim 1, further comprising a sensing element or system in fluid communication therewith.

18. The system of claim 17, wherein said sensing element or system comprises a nanostructure having covalently attached thereto said capturing moiety and is configured such that upon interaction of said capturing moiety and said analyte, a detectable signal which is indicative of a presence and/or level of said analyte is generated.

19. A method of extracting an analyte from a liquid containing same, the method comprising:
contacting the liquid with the system of claim 1 to thereby obtain a system having said analyte adsorbed to said nanostructures; and
exposing the system to light at a wavelength that generates said reactive moiety, thereby extracting the analyte from the liquid.

20. The method of claim 19, wherein said exposing is for a time period that ranges from 1 to 1000, or from 1 to 500, or from 1 to 100, seconds.

21. The method of claim 19, wherein said liquid is a biological sample.

22. The method of claim 19, wherein a concentration of the analyte in the liquid is less than 1 mM, or lower than 1 µM, or lower than 1 nM, or lower than 1 pM.

23. A method of determining a presence and/or a level of an analyte in a liquid, the method comprising:
subjecting the liquid to the method of claim 19; and
contacting the aqueous solution obtained upon said exposing with a sensing element or system configured for identifying and/or determining a presence and/or level of the analyte.

24. The method of claim 23, wherein said sensing element or system is in fluid communication with said system.

25. The method of claim 23, wherein said sensing element or system comprises a nanostructure having covalently attached thereto said capturing moiety and is configured such that upon interaction of said capturing moiety and said analyte, a detectable signal which is indicative of a presence and/or level of said analyte is generated.

* * * * *